(12) United States Patent
Frankle

(10) Patent No.: US 10,143,558 B2
(45) Date of Patent: Dec. 4, 2018

(54) SHOULDER ARTHROPLASTY SYSTEMS AND CONFIGURATIONS FOR COMPONENTS THEREOF

(71) Applicant: ENCORE MEDICAL, LP, Austin, TX (US)

(72) Inventor: Mark Frankle, Tampa, FL (US)

(73) Assignee: ENCORE MEDICAL, LP, Austin, TX (US)

( * ) Notice: Subject to any disclaimer, the term of this patent is extended or adjusted under 35 U.S.C. 154(b) by 232 days.

(21) Appl. No.: 15/384,048

(22) Filed: Dec. 19, 2016

(65) Prior Publication Data

US 2017/0095339 A1  Apr. 6, 2017

Related U.S. Application Data

(60) Continuation of application No. 14/271,214, filed on May 6, 2014, now Pat. No. 9,522,067, which is a
(Continued)

(51) Int. Cl.
*A61F 2/40* (2006.01)
*A61F 2/30* (2006.01)
(Continued)

(52) U.S. Cl.
CPC .............. *A61F 2/40* (2013.01); *A61F 2/4014* (2013.01); *A61F 2/4059* (2013.01); *A61F 2/4081* (2013.01); *A61F 2/30721* (2013.01); *A61F 2/30771* (2013.01); *A61F 2/4612* (2013.01); *A61F 2002/2835* (2013.01); *A61F 2002/2853* (2013.01); *A61F 2002/305* (2013.01); *A61F 2002/3006* (2013.01); *A61F 2002/3085* (2013.01); *A61F 2002/30115* (2013.01); *A61F 2002/30123* (2013.01); *A61F 2002/30125* (2013.01); *A61F 2002/30126* (2013.01);
(Continued)

(58) Field of Classification Search
CPC ...... A61F 2002/4085; A61F 2002/3453; A61F 2002/3483; A61F 2002/3615; A61F 2/4202–2002/4207; A61F 2/4261–2002/4297
See application file for complete search history.

(56) References Cited

U.S. PATENT DOCUMENTS 5,800,551 A  9/1998 Williamson et al.
6,306,172 B1  10/2001 O'Neil et al.
(Continued)

OTHER PUBLICATIONS

Depuy International Ltd., Delta CTA Reverse Shoulder Prosthesis, Surgical Technique Document, p. 1-28.
(Continued)

*Primary Examiner* — Yashita Sharma
*Assistant Examiner* — Rebecca Preston
(74) *Attorney, Agent, or Firm* — Veros Legal Solutions, LLP

(57) ABSTRACT

Shoulder arthroplasty systems and configurations for components thereof are described. For example, implant systems for a total should arthroplasty (TSA), hemi shoulder arthroplasty, and reverse should arthroplasty (RSA) are described. In addition, exemplary configurations for baseplates, glenoid components, glenosphere components, humeral components, humeral head components, humerosocket components, connectors, and adaptors, are described.

20 Claims, 25 Drawing Sheets

Related U.S. Application Data division of application No. 13/239,228, filed on Sep. 21, 2011.

(60) Provisional application No. 61/476,263, filed on Apr. 16, 2011, provisional application No. 61/442,272, filed on Feb. 13, 2011.

(51) Int. Cl.
  *A61F 2/46* (2006.01)
  *A61F 2/28* (2006.01)
  *A61L 27/28* (2006.01)

(52) U.S. Cl.
  CPC .............. *A61F 2002/30159* (2013.01); *A61F 2002/30242* (2013.01); *A61F 2002/30247* (2013.01); *A61F 2002/30332* (2013.01); *A61F 2002/30339* (2013.01); *A61F 2002/30365* (2013.01); *A61F 2002/30367* (2013.01); *A61F 2002/30377* (2013.01); *A61F 2002/30378* (2013.01); *A61F 2002/30405* (2013.01); *A61F 2002/30426* (2013.01); *A61F 2002/30433* (2013.01); *A61F 2002/30434* (2013.01); *A61F 2002/30578* (2013.01); *A61F 2002/30604* (2013.01); *A61F 2002/30607* (2013.01); *A61F 2002/30616* (2013.01); *A61F 2002/30649* (2013.01); *A61F 2002/30654* (2013.01); *A61F 2002/30772* (2013.01); *A61F 2002/4022* (2013.01); *A61F 2002/4085* (2013.01); *A61F 2220/0033* (2013.01); *A61F 2220/0041* (2013.01); *A61F 2310/00023* (2013.01); *A61F 2310/00029* (2013.01); *A61F 2310/00179* (2013.01); *A61F 2310/00592* (2013.01); *A61F 2310/00796* (2013.01); *A61L 27/28* (2013.01)

(56) References Cited

U.S. PATENT DOCUMENTS

| | | |
|---|---|---|
| 6,464,728 B1 | 10/2002 | Murray |
| 6,508,840 B1 | 1/2003 | Rockwood et al. |
| 6,514,287 B2 | 2/2003 | Ondrla et al. |
| 6,679,916 B1 | 1/2004 | Frankle et al. |
| 6,783,549 B1 | 8/2004 | Stone et al. |
| 6,790,234 B1 | 9/2004 | Frankle |
| 6,875,234 B2 | 4/2005 | Lipman et al. |
| 6,942,699 B2 | 9/2005 | Stone et al. |
| 7,044,973 B2 | 5/2006 | Rockwood et al. |
| 7,431,736 B2 | 10/2008 | Maroney et al. |
| 7,445,638 B2 | 11/2008 | Beguin et al. |
| 7,604,665 B2 | 10/2009 | Iannotti et al. |
| 7,699,853 B2 | 4/2010 | Durand-Allen et al. |
| 7,854,768 B2 | 12/2010 | Wiley et al. |
| 2001/0047210 A1 | 11/2001 | Wolf |
| 2002/0016634 A1 | 2/2002 | Maroney et al. |
| 2003/0100952 A1 | 5/2003 | Rockwood et al. |
| 2004/0122520 A1 | 6/2004 | Lipman et al. |
| 2004/0210317 A1 | 10/2004 | Maroney et al. |
| 2004/0220674 A1 | 11/2004 | Pria |
| 2004/0236428 A1 | 11/2004 | Burkinshaw et al. |
| 2005/0245808 A1 | 11/2005 | Carson |
| 2006/0069445 A1 | 3/2006 | Ondrla et al. |
| 2006/0276905 A1 | 12/2006 | Calamel |
| 2007/0173945 A1 | 7/2007 | Wiley et al. |
| 2007/0260321 A1 | 11/2007 | Stchur |
| 2008/0208348 A1 | 8/2008 | Fitz |
| 2009/0062923 A1 | 3/2009 | Swanson |
| 2009/0125113 A1 | 5/2009 | Guederian et al. |
| 2009/0192621 A1 | 7/2009 | Winslow et al. |
| 2010/0016975 A1 | 1/2010 | Iannotti et al. |
| 2010/0137925 A1 | 6/2010 | Durand-Allen et al. |
| 2010/0217399 A1 | 8/2010 | Groh |
| 2010/0222886 A1 | 9/2010 | Wiley et al. |
| 2010/0234965 A1 | 9/2010 | Pria et al. |
| 2010/0241235 A1 | 9/2010 | Basamania et al. |
| 2012/0253467 A1 | 10/2012 | Frankle |
| 2014/0243986 A1 | 8/2014 | Frankle |

OTHER PUBLICATIONS

Depuy International Ltd., Delta Xtend Reverse Shoulder System, Surgical Technique Document, p. 1-58.

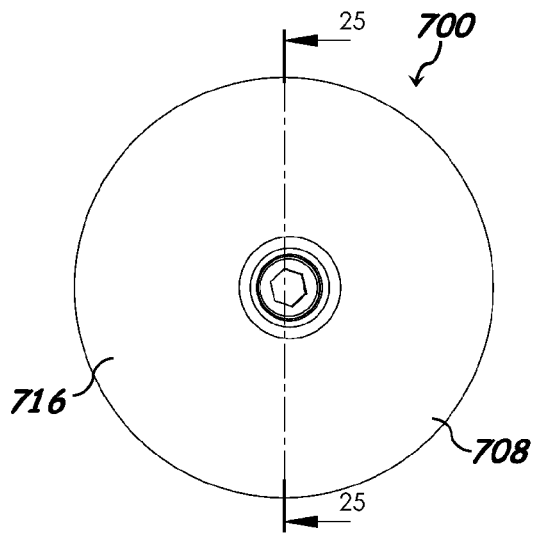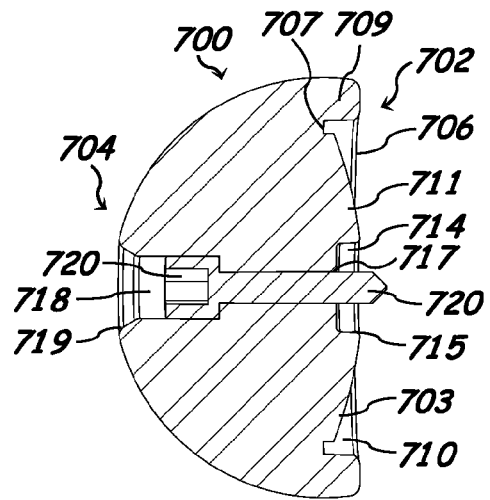
Figure 24         Figure 25
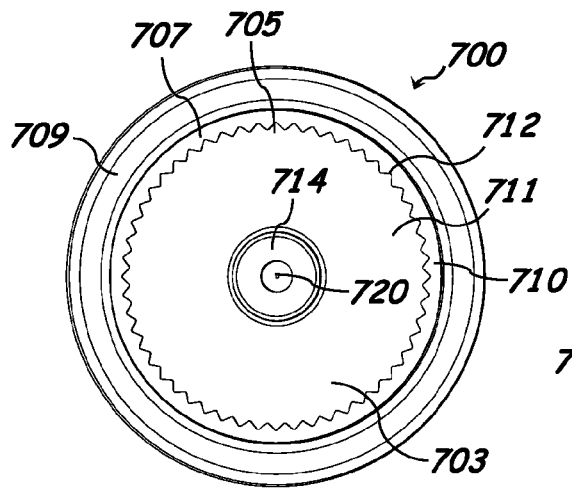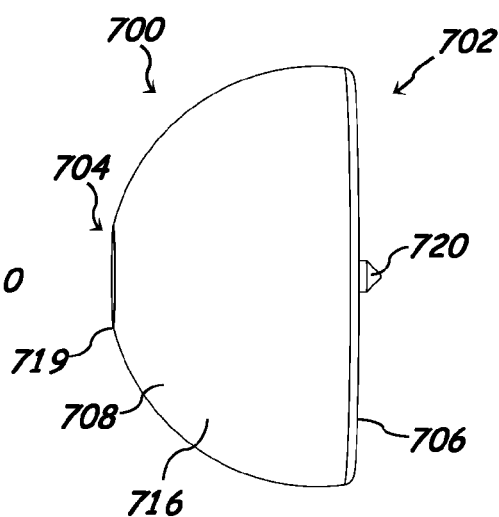
Figure 26         Figure 27

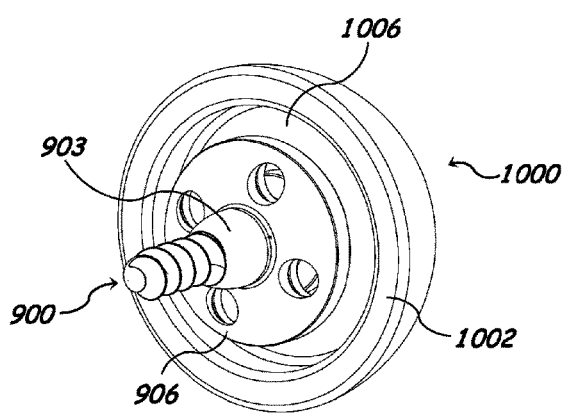
Figure 33
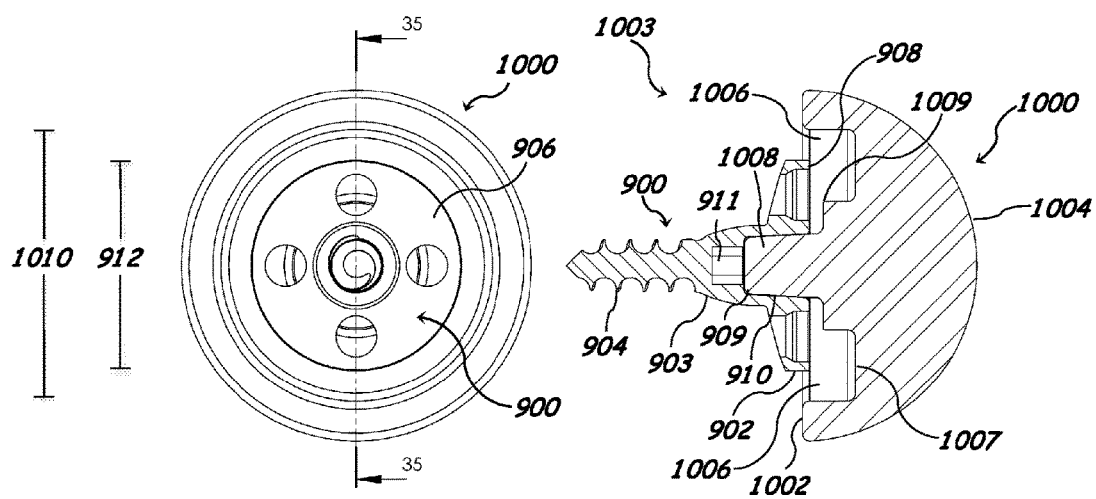
Figure 34
Figure 35

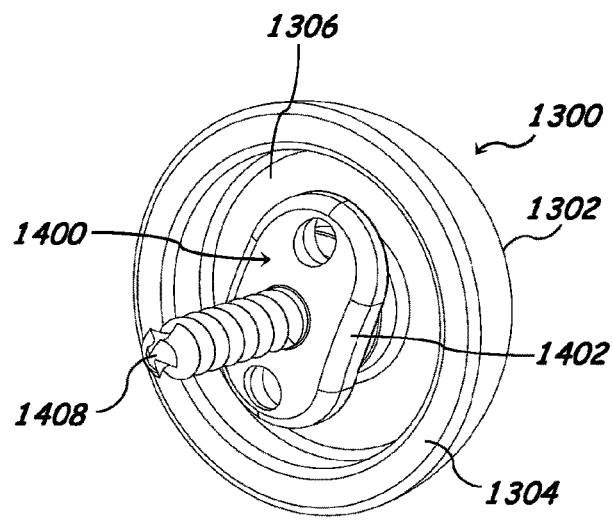
*Figure 41*
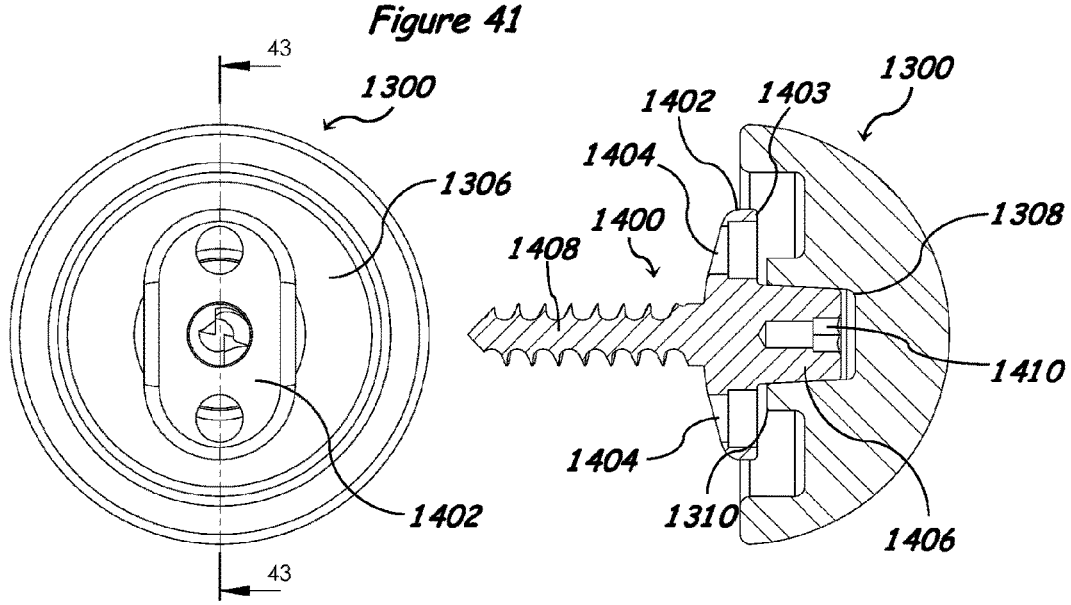
*Figure 42*          *Figure 43*

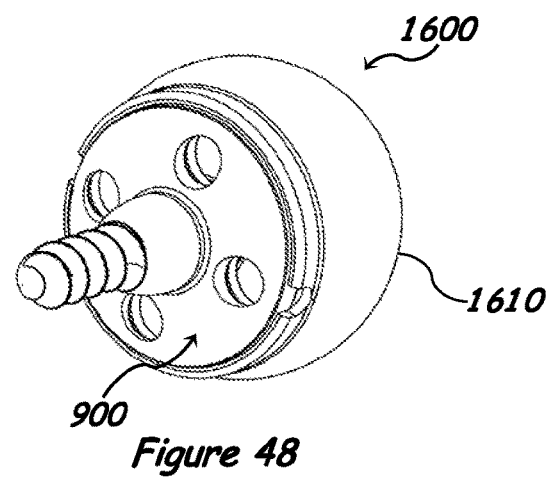
Figure 48
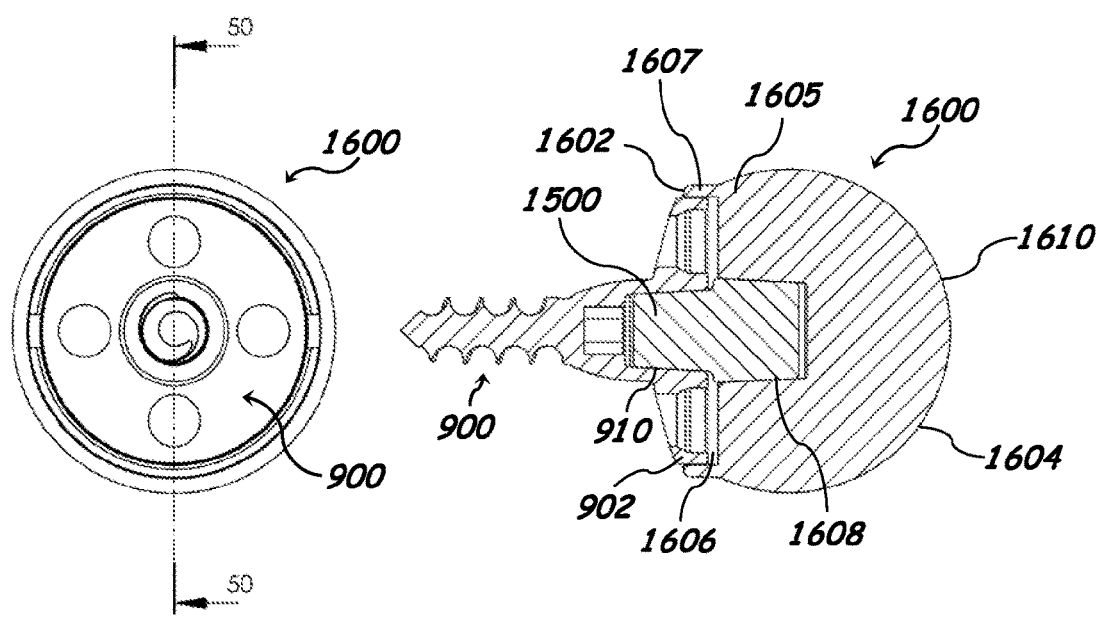
Figure 49
Figure 50

SHOULDER ARTHROPLASTY SYSTEMS AND CONFIGURATIONS FOR COMPONENTS THEREOF

CROSS-REFERENCE TO RELATED APPLICATIONS

This application is a continuation of U.S. application Ser. No. 14/271,214, filed May 6, 2014, now U.S. Pat. No. 9,522,067 which is a Divisional of U.S. application Ser. No. 13/239,228, filed Sep. 21, 2011, which claims the benefit of U.S. Provisional Application No. 61/442,272, filed Feb. 13, 2011 (entitled "Unique Convertible Design for Total Shoulder Arthroplasty") and which also claims the benefit of U.S. Provisional Application No. 61/476,263, filed Apr. 16, 2011 (entitled "Unique Baseplate, Glenosphere and Replacement Humeral Head Designs for Reverse, Total or Hemi Shoulder Arthroplasty"). Each of the above-referenced applications is hereby incorporated by reference into this disclosure in its entirety.

BACKGROUND OF THE INVENTION

Field of the Invention

The invention relates generally to surgical implant systems. More particularly, the invention relates to shoulder arthroplasty systems and configurations for the components thereof.

Description of the Related Technology

It has become common to perform a shoulder arthroplasty to repair a patient's shoulder joint that has become dysfunctional due to disease or trauma. In a healthy shoulder, the humeral head is generally ball-shaped, and articulates within a socket formed by the scapula, called the glenoid cavity, to form the shoulder joint. Conventional implant systems for the total replacement of the shoulder joint (e.g., total shoulder arthroplasty (TSA)) generally replicate the natural anatomy of the shoulder, and include a metal humeral component having a stem which fits within the humeral canal, and an articulating head which articulates within the socket of a plastic glenoid component implanted within the glenoid of the scapula. The glenoid component can be either a single piece component that is attached to the glenoid, or a two-piece component having a plastic glenoid component attached to a metal baseplate, which is attached to the glenoid. In some cases, however, it is only necessary to replace a part of the shoulder joint, for example, by replacing the humeral head (e.g., a hemi shoulder arthroplasty (HAS)) with a prosthetic humeral head to articulate within the natural glenoid cavity of the scapula.

Recently, "reverse" type implant systems (e.g., total reverse shoulder arthroplasty (RSA)) have been developed in which the conventional ball-and-socket configuration that replicates the natural anatomy of the shoulder is reversed, such that a concave recessed articulating component is provided at the proximal end of the humeral component which articulates against a convex portion of a glenoid component. Such reverse shoulder implant systems are thought to provide an increased range of motion for treatment of glenoid humeral arthritis associated with irreparable rotator cuff damage, for example, by moving the center of rotation between the humeral component and the glenoid component to allow the deltoid muscles to exert a greater lever arm on the humerus.

It is sometimes necessary to convert from one type of implant system (e.g., TSA) to the other type of implant system (e.g., RSA), for example, when a patient does not react positively to an initially implanted system. Furthermore, it is sometimes necessary to replace components that have been implanted and are not functioning properly. Therefore, a need exists for arthroplasty systems and configurations of the components thereof.

SUMMARY

Various shoulder arthroplasty systems are described herein. For example, an exemplary baseplate and humeral component are described which allow for the conversion between a TSA to an RSA, or vice versa. In addition, exemplary configurations for a baseplate, glenoid component, glenosphere component, humeral component, humeral head component, humerosocket component, connector, and adaptor are described. Furthermore, exemplary positioning of osteoinductive material is described to assist in the stability of the components.

Additional understanding of the systems and configurations contemplated and/or claimed by the inventor can be gained by reviewing the detailed description of exemplary embodiments, presented below, and the referenced drawings.

BRIEF DESCRIPTION OF THE DRAWINGS

FIG. 24 is a front elevation view of an exemplary glenosphere component.

FIG. 25 is a cross-sectional view of the glenosphere component illustrated in FIG. 24, taken along line 25-25 in FIG. 24.

FIG. 26 is a rear elevation view of the glenosphere component illustrated in FIG. 24.

FIG. 27 is a side elevation view of the glenosphere component illustrated in FIG. 24.

FIG. 33 is a perspective view of another exemplary glenosphere component attached to another exemplary baseplate.

FIG. 34 is a rear elevation view of the glenosphere component illustrated in FIG. 33 attached to the baseplate illustrated in FIG. 33.

FIG. 35 is a cross-sectional view of the glenosphere component illustrated in FIG. 33 attached to the baseplate illustrated in FIG. 33, taken along line 35-35 in FIG. 34.

FIG. 41 is a perspective view of another exemplary glenosphere component attached to another exemplary baseplate.

FIG. 42 is a rear elevation view of the glenosphere component illustrated in FIG. 41 attached to the baseplate illustrated in FIG. 41.

FIG. 43 is a cross-sectional view of the glenosphere component illustrated in FIG. 41 attached to the baseplate illustrated in FIG. 41, taken along line 43-43 in FIG. 42.

FIG. 48 is a perspective view of another exemplary glenosphere component attached to the baseplate illustrated in FIG. 33 using the connector illustrated in FIG. 44.

FIG. 49 is a rear elevation view of the glenosphere component illustrated in FIG. 48 attached to the baseplate illustrated in FIG. 33 using the connector illustrated in FIG. 44.

FIG. 50 is a cross-sectional view of the glenosphere component illustrated in FIG. 48 attached to the baseplate illustrated in FIG. 33 using the connector illustrated in FIG. 44, taken along line 50-50 in FIG. 49.

DETAILED DESCRIPTION OF CERTAIN INVENTIVE EMBODIMENTS

The following detailed description and the appended figures are provided to describe and illustrate exemplary embodiments of the invention for the purpose of enabling one of ordinary skill in the relevant art to make and use the invention. The description and figures are not intended to limit the scope of the invention, or its protection, in any manner.

As used herein the terms "proximal" and "distal" are used to describe opposing axial ends of the particular elements, components, or features being described. The term "attached" refers to the fixed, releasable, or integrated association of two or more elements, components, and/or devices. The term "attached" includes releasably attaching or fixedly attaching two or more elements, components, and/or devices. The terms "medial" and "lateral" are used to describe opposing sides of the particular elements, components, or features being described. The singular forms "a," "an," and "the" include plural referents unless the context clearly dictates otherwise.

Figure 1:
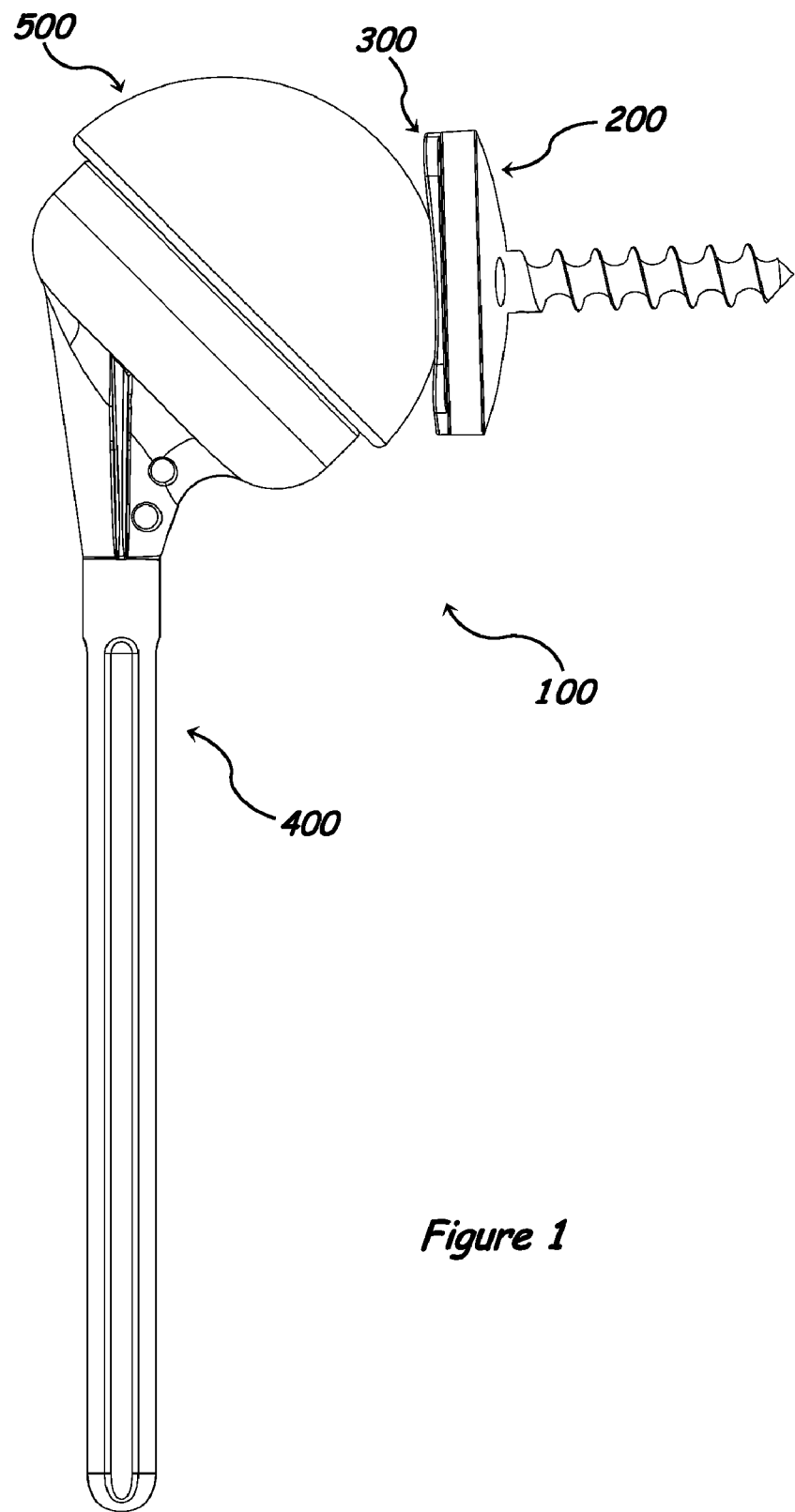
FIG. 1 is a side elevation view of an exemplary TSA system.
Figures 2, 3:
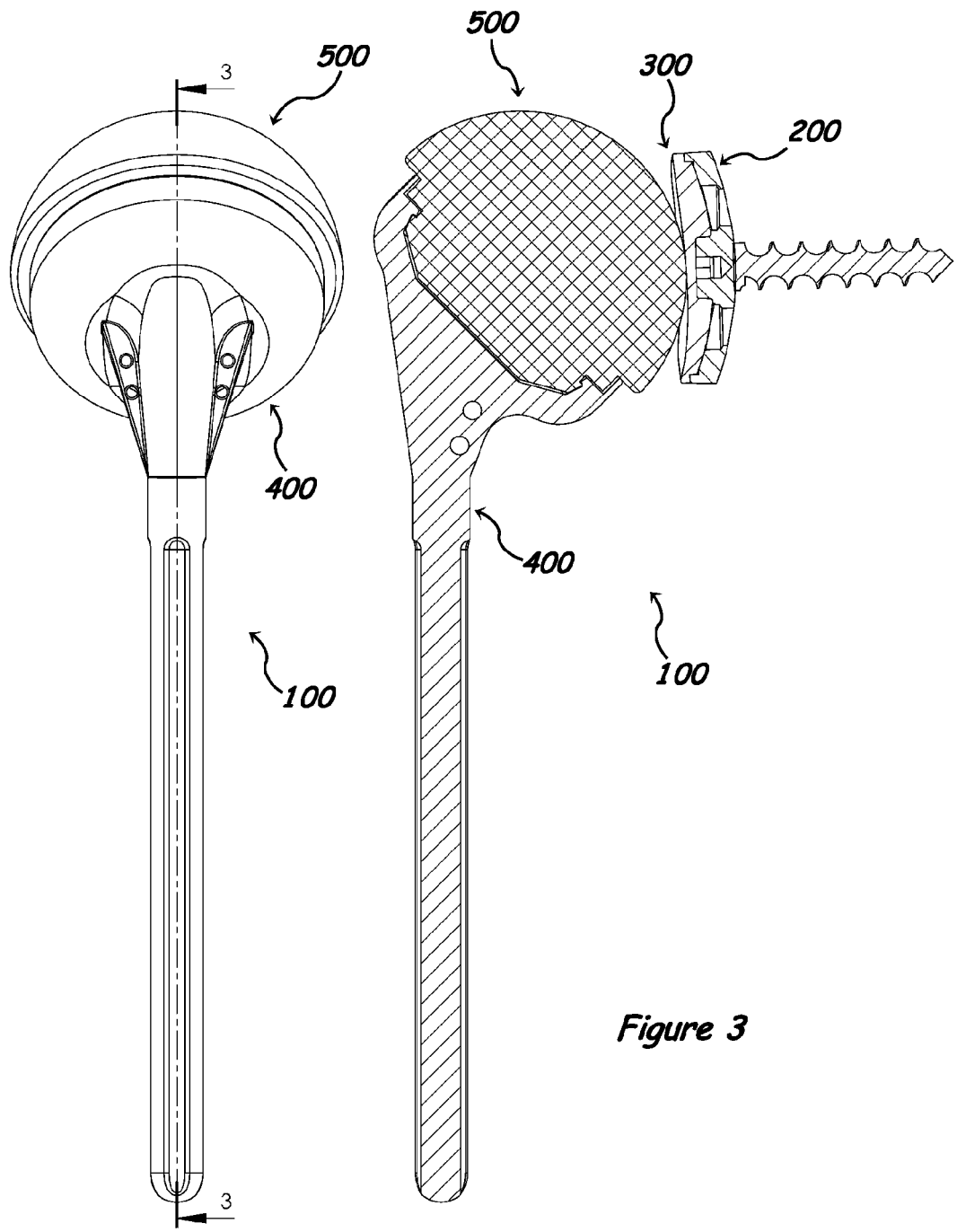
FIG. 2 is a rear elevation view of the TSA system illustrated in FIG. 1.
FIG. 3 is a cross-sectional view of the TSA system illustrated in FIG. 1, taken along line 3-3 in FIG. 2.
Figure 4:
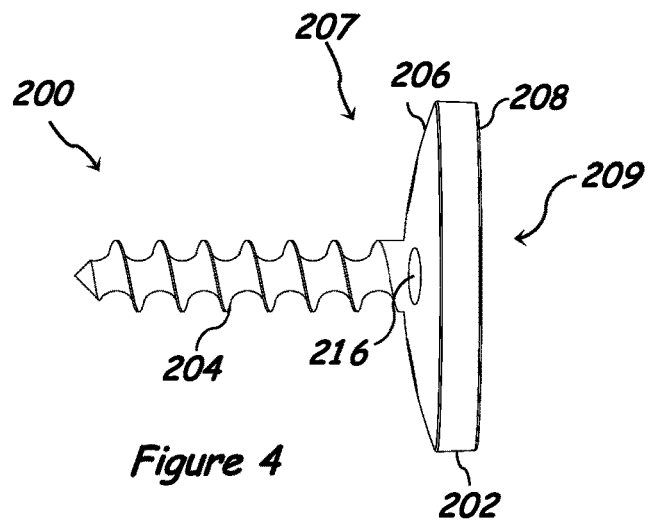
FIG. 4 is a side elevation view of an exemplary baseplate.
Figures 5, 6:
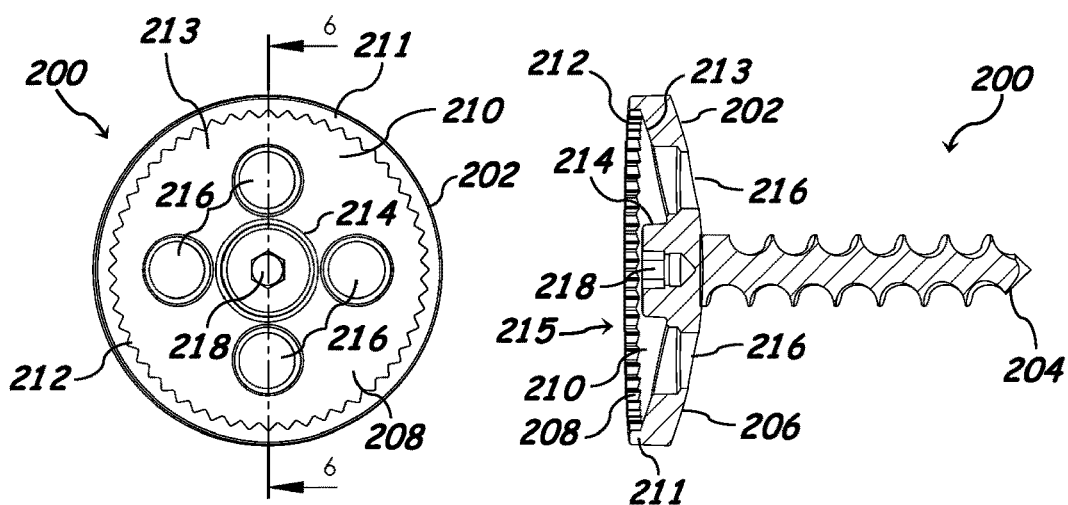
FIG. 5 is a front elevation view of the baseplate illustrated in FIG. 4.
FIG. 6 is a cross-sectional view of the baseplate illustrated in FIG. 4, taken along line 6-6 in FIG. 5.
Figure 7:
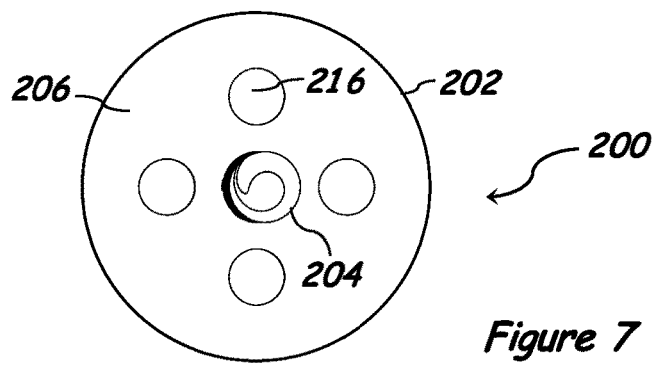
FIG. 7 is a rear elevation view of the baseplate illustrated in FIG. 4.
Figure 8:
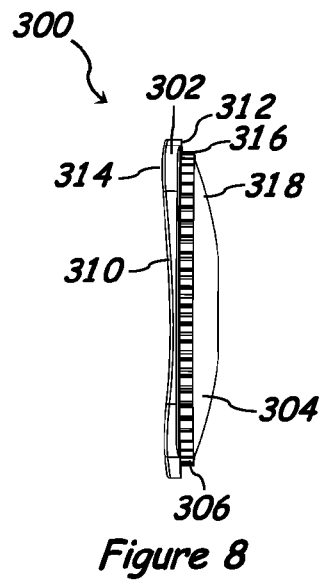
FIG. 8 is a side elevation view of an exemplary glenoid component.
Figure 9:
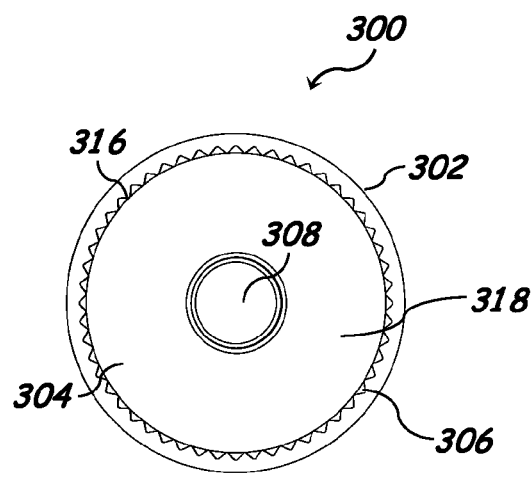
FIG. 9 is a rear elevation view of the glenoid component illustrated in FIG. 8.
Figure 10:
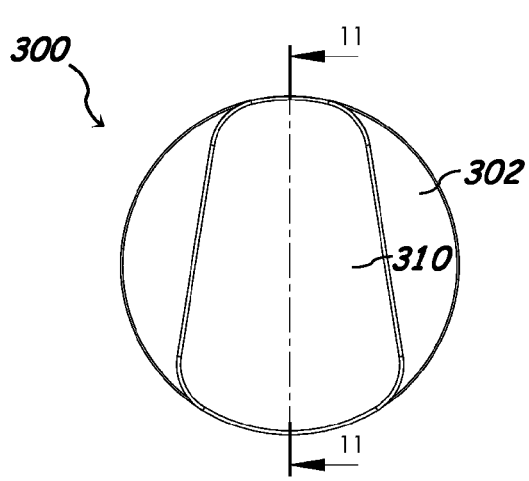
FIG. 10 is a front elevation view of the glenoid component illustrated in FIG. 8.
Figure 11:
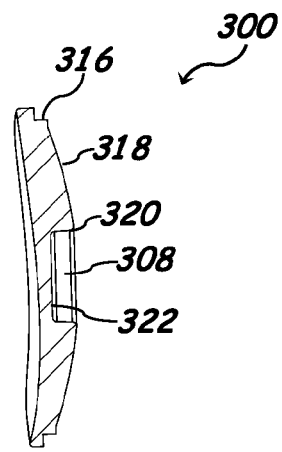
FIG. 11 is a cross-sectional view of the glenoid component illustrated in FIG. 8, taken along line 11-11 in FIG. 10.

FIGS. 1 through 3 illustrate an exemplary TSA system 100 comprising a baseplate 200, a glenoid component 300, a humeral component 400, and a humeral head component 500. The baseplate 200 is configured to be received by, and attached to, a previously prepared scapula of a patient and the glenoid component 300 is configured to be received by, and attached to, the baseplate 200. The humeral component 400 is configured to be received by, and attached to, a previously prepared humerus of a patient and the humeral head component 500 is configured to be received by, and attached to, the humeral component 400.

FIGS. 4 through 7 illustrate an exemplary baseplate 200 comprising a body 202 and a threaded component 204. The body 202 is generally circular, has a thickness, and comprises a medial side 206, lateral side 208, proximal end 207, distal end 209, recess 210, circumferential, or substantially circumferential, wall 211, toothed geometry 212, base 213, tapered trunnion 214, and bores 216. The medial side 206 of the body 202 is convex, or substantially convex, and has threaded component 204 attached thereto. Both the medial side 206 of the baseplate 200 and the threaded component 204, or portions thereof, are adapted to be received by, and attached to, a previously prepared scapula of a patient. While the medial side 206 has been described and illustrated as convex, or substantially convex, any suitable geometry can be used, and skilled artisans will be able to select an appropriate geometry for a particular embodiment based on various considerations, including the size and condition of the patient's scapula, among others. Examples of suitable geometries include flat, concave, and variating surfaces.

Optionally, a portion, or the entirety of, the medial side 206 of the body 202 can include a textured surface, and/or osteoinductive surface, (not shown) to increase the strength, fixation, stability, and securement of the baseplate 200 to the scapula of a patient. The textured surface can include one or more protuberances, bumps, groves, and/or a roughened surface in any configuration and/or combination.

The threaded component 204 comprises a threaded shank that extends proximally, and away, from the lateral side 208 of the body 202. The threads can be formed on the shank and extend from the proximal end to the distal end of the threaded component 204. Alternatively, the threads can begin at a point between the proximal end and the distal end of the threaded component 204 and extend to the proximal end of the threaded component 204. In a further alternative, the threaded component 204 can include an enlarged distal end (e.g., shaft 903 of baseplate 900) to assist with attachment of the component to the scapula of a patient.

The threaded component 204 can have any suitable length, diameter, number of threads, and can be positioned in any suitable location and at any suitable angle on the medial side 206 of the body 202, and skilled artisans will be able to select an appropriate threaded component, position, and angle according to a particular embodiment based on various considerations, including the size and condition of the patient's scapula, among others. In addition, while a threaded component 204 has been illustrated as attached to the medial side 206 of the body 202, any suitable attachment mechanism suitable for securing the baseplate 200 to a scapula can be utilized (e.g., attachment pegs, Morse taper). The threaded component 204 can be attached, fixedly attached, removably attached, integral with, or separate from the baseplate 200. It is considered advantageous to provide a threaded component 204 that is integral with the baseplate 200 to increase the structural stability of the baseplate 200 and its attachment to the scapula of a patient.

The wall 211 and base 213 cooperatively define recess 210 that extends proximally into the thickness of the body 202 from the lateral side 208 towards the medial side 206. The wall 211 forms toothed geometry 212 that extends about the entirety, or a portion of, the wall 211 and radially inward towards the center of the baseplate 200. Base 213 has a concave, or substantially concave, configuration and extends from the wall 211 towards the medial side 206.

While the wall 211 has been described as circumferential, or substantially circumferential, other configurations are considered suitable, and skilled artisans will be able to select an appropriate configuration according to a particular embodiment based on various considerations, such as the configuration of the glenoid component 300, among others. An example of a configuration of wall that is considered suitable includes a wall that partially extends around the circumference of the body of the baseplate. In addition, while the toothed geometry 212 has been described as extending into recess 210, other configurations are considered suitable, and the depth and length provided between each tooth of the toothed geometry 212, the number of teeth, and the angle at which the teeth are disposed on the wall 211 of the recessed portion 210 can vary, and skilled artisans will be able to select an appropriate configuration according to a particular embodiment based on various considerations, including the size and/or configuration of the baseplate and glenoid component. Furthermore, while base 213 has been described and illustrated as being concave, or substantially concave, any suitable geometry can be used, and skilled artisans will be able to select an appropriate geometry for a particular embodiment based on various considerations, including the geometry of the medial side of the body, and/or the geometry of the medial side of the glenoid component, among others. Examples of suitable geometries include flat, convex, and variating surfaces.

Tapered trunnion 214 (e.g., Morse taper) is disposed on the base 213 of the body 202, extends from the base 213 towards the first lateral side, and tapers from its base to its distal end 215. The tapered trunnion 214 defines a hexagonal recess 218 at, or near, the center of the distal end 215, which extends proximally into the tapered trunnion 214 away from the lateral side 208, and is adapted to receive a tool used to assist with installing the baseplate 200 into the scapula of a patient. The tapered trunnion 214 can include one or more annular ribs, protuberances, and/or raised surfaces (not shown) to increase stability of the component when another component is attached thereto. While a hexagonal recess 218 has been illustrated as defined by the tapered trunnion 214, any suitable geometrical shape can be defined by the tapered trunnion 214, and skilled artisans will be able to select an appropriate geometrical shape for a particular embodiment based on various considerations, such as the depth of the tapered trunnion, among others.

Bores 216 are positioned between the tapered trunnion 214 and toothed geometry 212 and extend through the thickness of the body 202 from the medial side 206 to the lateral side 208. The bores 216 are equidistantly spaced about the tapered trunnion 214 and allow for one or more fasteners to have a length inserted through the bores 216 and into the scapula of a patient, assisting with securing the baseplate 200 to the scapula of a patient. While four bores 216 have been illustrated equidistantly spaced about the tapered trunnion, any suitable number of bores and configuration can be incorporated into the baseplate, and skilled artisans will be able to select an appropriate number of bores for a particular embodiment based on various considerations, such as the size of the scapula, among others. Examples of suitable numbers of bores include one, two, three, four, five, six and any number determined suitable for a particular application. Alternatively, bores 216 can be omitted.

Figure 21:
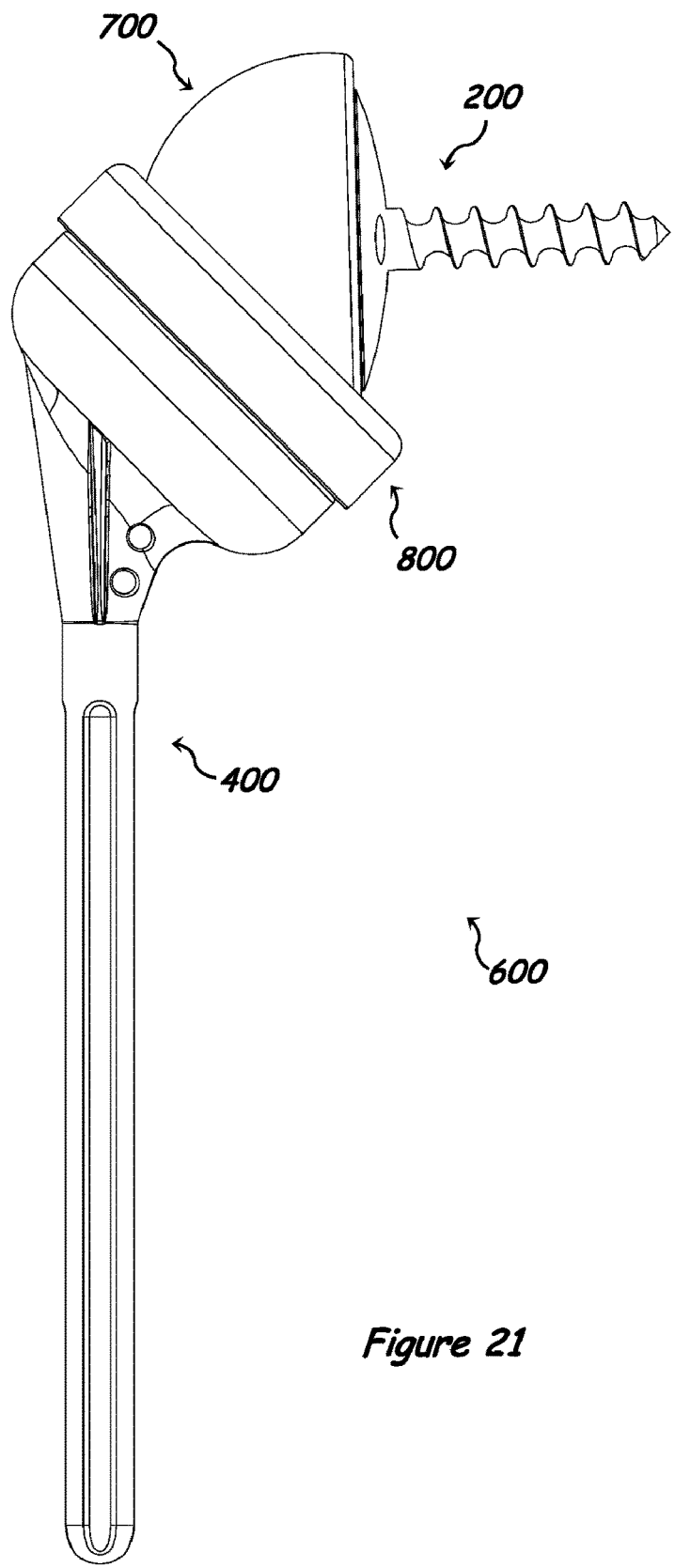
FIG. 21 is a side elevation view of an exemplary RSA system.
Figures 22, 23:
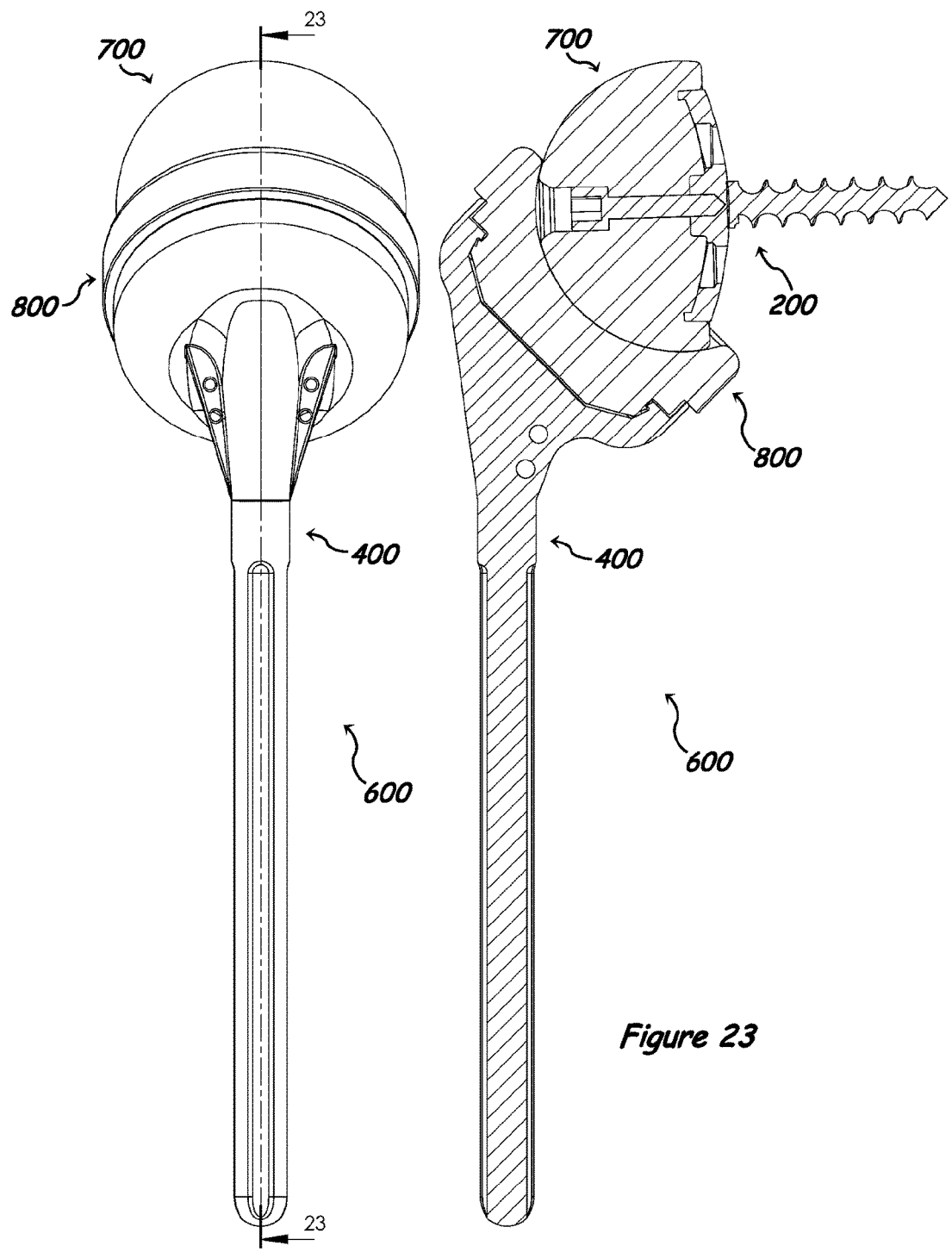
FIG. 22 is a rear elevation view of the RSA system illustrated in FIG. 21.
FIG. 23 is a cross-sectional view of the RSA system illustrated in FIG. 21, taken along line 23-23 in FIG. 22.

The baseplate 200 is formed of a metal, alloy, or any other suitable biocompatible material. Exemplary materials considered suitable for the baseplate include titanium (Ti), cobalt-chromium-molybdenum (CoCrMo) and other cobalt alloys (e.g., cobalt-chromium (CoCr). The baseplate 200 advantageously provides a component that serves as a universal platform that may be used with various modular components (e.g., glenoid component 300, glenosphere component 700) in the manner described herein to configure the baseplate 200 for use in a TSA or a RSA. Thus, once the baseplate 200 is implanted onto the scapula of a patient, the baseplate 200 can be configured for a TSA as illustrated in FIGS. 1 through 3, or a RSA as illustrated in FIGS. 21 through 23. While the baseplate 200 has been described as formed of a metal, alloy, or other suitable biocompatible material, other materials are considered suitable, and skilled artisans will be able to select an appropriate material according to a particular embodiment based on various considerations, such as the intended use of the baseplate, among others.

FIGS. 8 through 11 illustrate an exemplary glenoid component 300 comprising a generally circular body 302, raised geometry 304, toothed geometry 306, tapered cavity 308 and an articulating surface 310. The body 302 has a medial side 312 and a lateral side 314 defining an articulating surface 310. The raised geometry 304 is disposed on the medial side 312 of the body 302, extends away from the lateral side 314 of the body 302, and has an outer circumferential, or substantially circumferential, perimeter 316 and a convex, or substantially convex, portion 318 that extends from the outer perimeter 316 and away from the lateral side 314. The toothed geometry 306 is formed on the outer perimeter 316 and extends about the entirety of, or a portion of, the perimeter 316 and radially outward away from the raised geometry 304.

The raised geometry 304 has a configuration that compliments the configuration of the recess 210 of the baseplate 200, and is adapted to be received by, and engage with, the geometry of the recess 210 of the baseplate 200. The toothed geometry 306 of the glenoid component 300 is configured to compliment the toothed geometry 212 of the baseplate 200 and is adapted to be received by, and engage with, the toothed geometry 212 of the baseplate 200. The depth and length provided between each tooth of the toothed geometry 306, the number of teeth, and the angle at which the teeth are disposed on the perimeter 316 of the raised geometry 304 can vary, and skilled artisans will be able to select an appropriate configuration according to a particular embodiment based on various considerations, including the size of the baseplate and glenoid component. While portion 318 has been described and illustrated as being convex, or substantially convex, any suitable geometry can be used, and skilled artisans will be able to select an appropriate geometry for a particular embodiment based on various considerations, including the geometry of the lateral side of the body of the baseplate, among others. Examples of suitable geometries include flat, concave, and variating surfaces.

In addition, while the raised geometry 304 is described as having a circumferential, or substantially circumferential, perimeter 316, other configurations are considered suitable, and skilled artisans will be able to select an appropriate configuration according to a particular embodiment based on various considerations, such as the configuration of the baseplate 200, among others. An example of a configuration for the raised geometry, and/or perimeter, that is considered suitable includes a raised geometry, and/or perimeter, that partially extends around the circumference of the body of the glenoid component.

The raised geometry 304 defines tapered cavity 308 which has an opening 320 defined on the convex, or substantially convex, portion 318. The tapered cavity 308 extends distally from the opening 320 into the raised geometry 304 and is tapered from the opening 320 to the base 322 of the tapered cavity 308. The tapered cavity 308 is adapted to receive the tapered trunnion 214 of the baseplate 200 (e.g., Morse taper) to attach the glenoid component 300 to the baseplate 200, and has a configuration complimentary to the tapered trunnion 214 of the baseplate 200.

The lateral side 314 of the glenoid component 300 defines a raised anatomically shaped articulating surface 310 configured to articulate with a humeral head (e.g., prosthetic or natural) of a patient. The articulating surface 310 is generally smooth, uninterrupted, and concave or substantially concave. The geometry of the articulating surface 310 is configured to approximate, and/or replicate, the anatomy and structure of the glenoid cavity of a patient (e.g., radius, thickness, length, width).

The glenoid component 300 is formed of a ceramic, metal, or other suitable biocompatible material. Exemplary materials considered suitable for the glenoid component 300 include titanium (Ti), and cobalt alloys (e.g., cobalt-chromium (CoCr), cobalt-chromium-molybdenum (CoCrMo)). It is considered advantageous to provide a glenoid component 300 formed of a metal to provide enhanced wear properties of the component. The glenoid component 300 is configured to be attached to the baseplate 200 using an impact instrument that impacts the tapered trunnion 214 of the baseplate 200 into the tapered cavity 308 of the glenoid component 300 creating a cold weld between the two components. The articulating surface 310, glenoid component 300, and/or baseplate 200, can be provided in a variety of different radii and/or sizes, such as with varying diameters, heights, and widths to enable a surgeon to select an optimal articulating surface 310, glenoid component 300 and/or baseplate 200 needed for the anatomy of a particular patient. While the glenoid component 300 has been described as formed of a ceramic, metal, or other suitable biocompatible material, other materials are considered suitable, and skilled artisans will be able to select an appropriate material according to a particular embodiment based on various considerations, such as the intended use of the glenoid component, among others.

Figure 12:
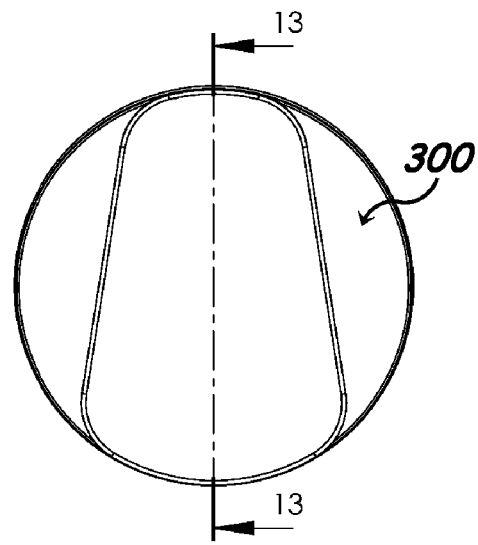
FIG. 12 is a front elevation view of the glenoid component illustrated in FIG. 8 attached to the baseplate illustrated in FIG. 4.
Figure 13:
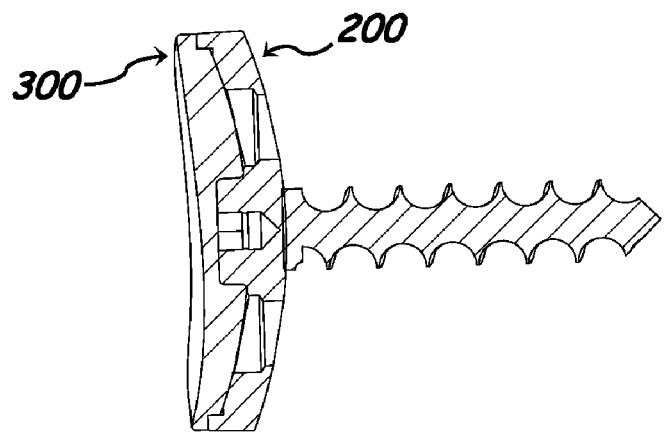
FIG. 13 is a cross-sectional view of the glenoid component illustrated in FIG. 8 attached to the baseplate illustrated in FIG. 4, taken along line 13-13 in FIG. 12.
Figure 14:
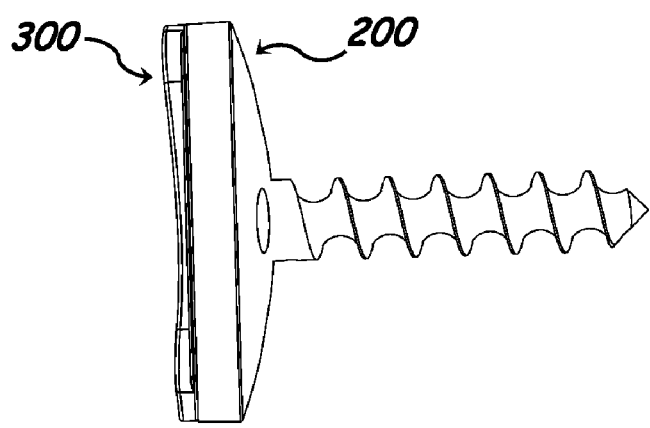
FIG. 14 is a side elevation view of the glenoid component illustrated in FIG. 8 attached to the baseplate illustrated in FIG. 4.

The toothed geometry 212 of the baseplate 200 and/or the toothed geometry 306 of the glenoid component 300 are adapted to receive one another, and include a tolerance sufficient to allow the components to properly engage with one another and become securely engaged, as illustrated in FIGS. 12 through 14, which advantageously provides a combination of components (e.g., glenoid implant) that prevents, or substantially limits, rotation subsequent to installation. In addition, the configuration of the toothed geometry 212 of the baseplate 200 and/or the toothed geometry 306 of the glenoid component 300 advantageously provide for rotationally variable positioning of the glenoid component 300 within the baseplate 200 when the two components are being attached to one another.

While the baseplate 200 and the glenoid component 300, or portions thereof, have been illustrated as circular, or substantially circular, other shapes are considered suitable, and skilled artisans will be able to select an appropriate shape for a baseplate and glenoid component according to a particular embodiment based on various considerations, including the anatomy of the patient, among others. Examples of shapes considered suitable include oval, oblong, rectangular and any shape determined suitable for a particular application.

Figure 15:
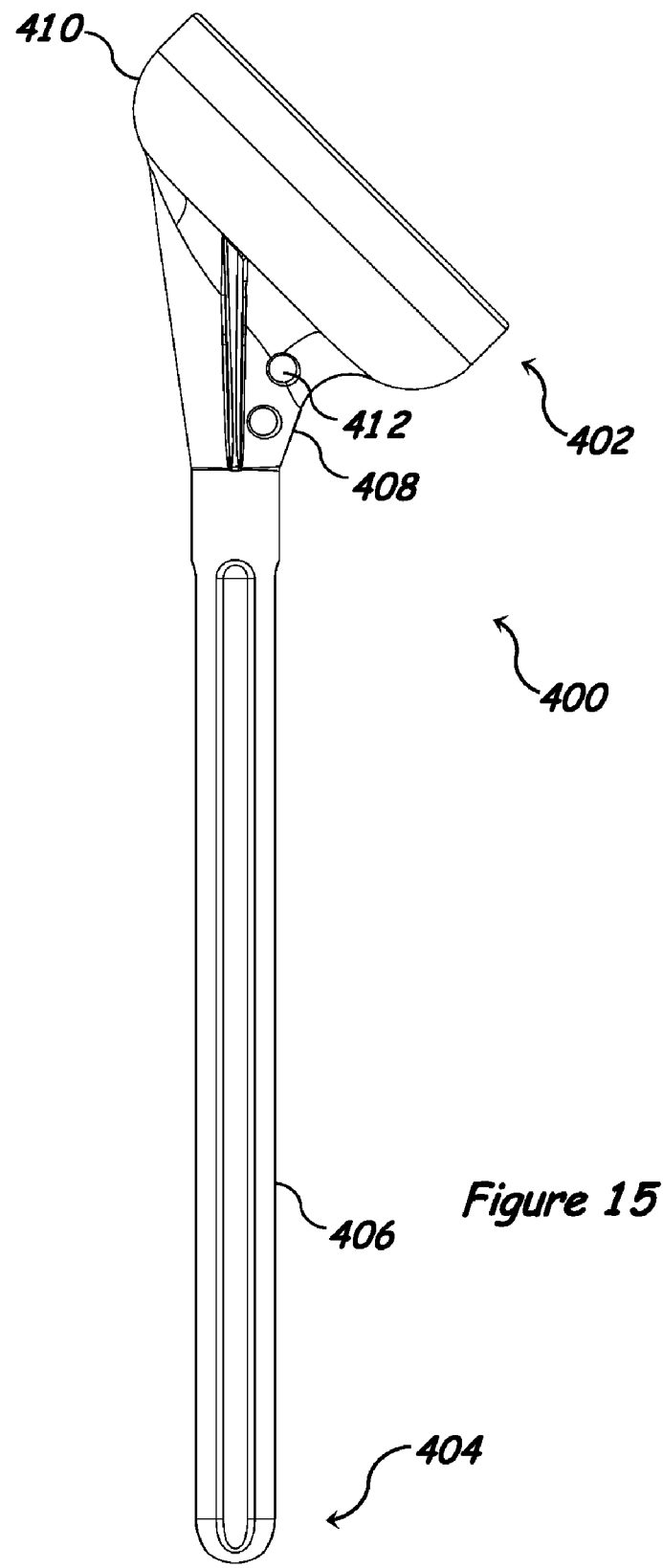
FIG. 15 is a side elevation view of an exemplary humeral component.
Figure 16:
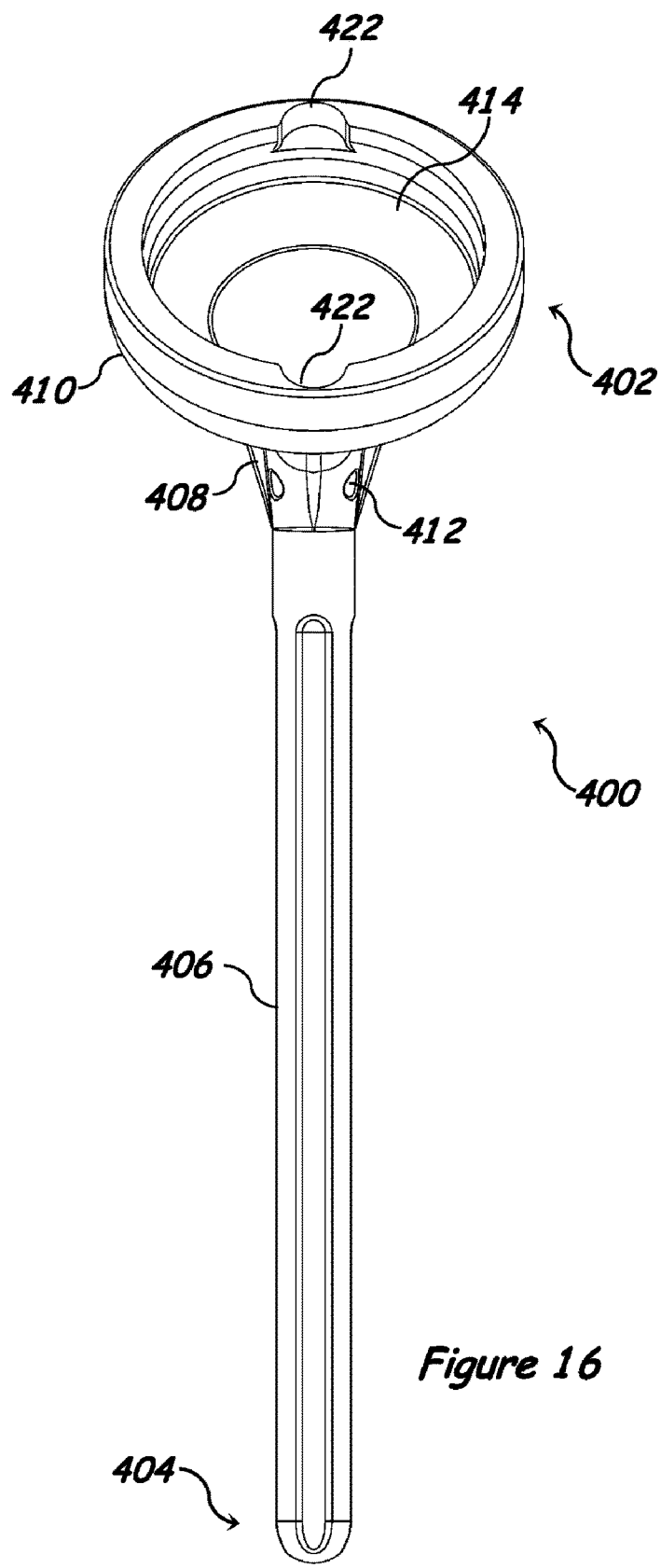
FIG. 16 is a front elevation view of the humeral component illustrated in FIG. 15.

FIGS. 15 and 16 illustrate an exemplary humeral component 400 comprising a proximal end 402, distal end 404, distal stem 406, transition region 408, and proximal head 410. The distal stem 406 extends from the distal end 404 to the transition region 408 and is adapted to be fitted within a prepared proximal end and canal of the humerus of a patient. The transition region 408 flares outwardly, and away, from the distal stem 406 and includes apertures 412 that extend through a portion of the transition region 408 of the humeral component 400. Sutures may be threaded through the apertures 412 to aid in reducing humeral fractures, or as otherwise needed. For example, the apertures 412 may be used by a physician to reconstruct the proximal humerus in the event of humeral fractures, for the attachment of soft tissue, and/or for the attachment of tuberosity fragments. The number of apertures 412 can vary, and skilled artisans will be able to select an appropriate number of apertures for a particular embodiment based on various considerations, including the intended use of the apertures, among others. Examples of suitable numbers of apertures include one, two, three, four, five, six, seven, eight, nine, ten and any number determined suitable for a particular application.

Figure 20:
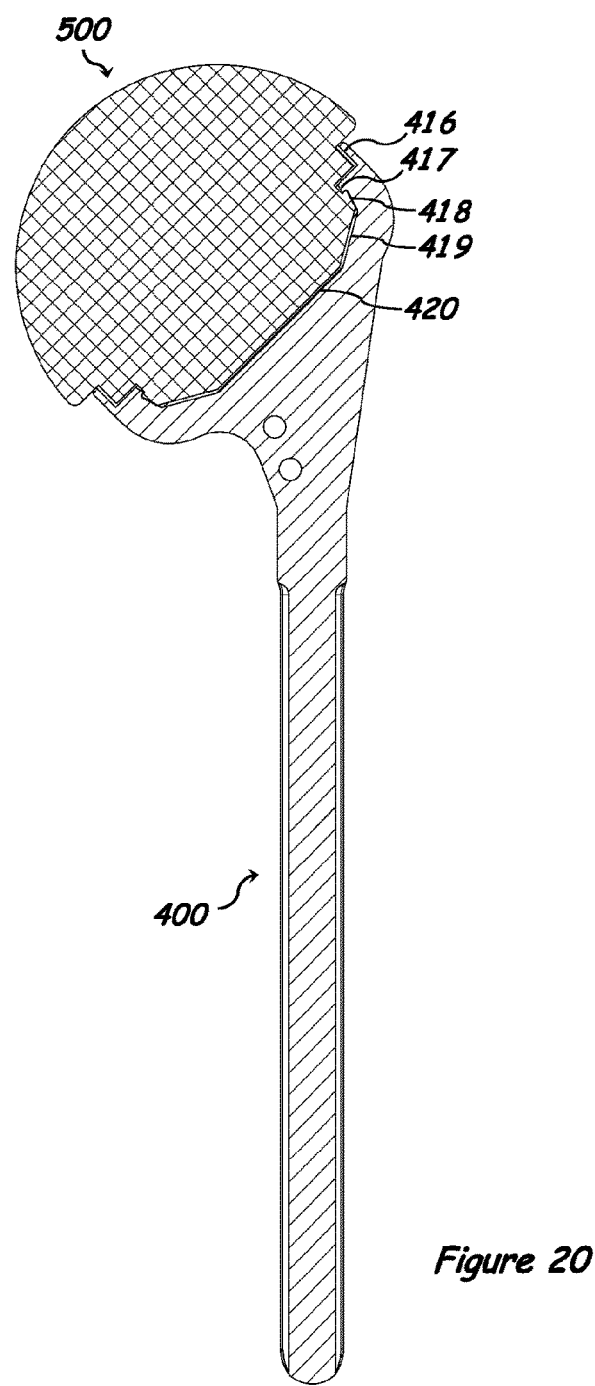
FIG. 20 is a cross-sectional view of the humeral head component illustrated in FIG. 17 attached to the humeral component illustrated in FIG. 15, taken along line 20-20 in FIG. 19.

Proximal head 410 is substantially enlarged with respect to the distal stem 406, flares outwardly from the transition region 408, and extends to the proximal end 402 of the humeral component 400. The proximal head 410 defines cavity 414 that extends distally into the proximal head 410 from the proximal end 402 of the humeral component 400. The cavity 414 has a first annular portion 416, lip 417, second annular portion 418, tapered portion 419, and base 420, as shown in FIG. 20. The first annular portion 416 is located at the proximal end of the cavity and extends distally into the proximal head 410 from the proximal end 402 of the humeral component 400 to lip 417, which extends radially inward towards the center of the internal cavity 414 and away from the wall of the proximal head 410. Distal to the lip 417 is second annular portion 418 that tapers from its proximal end at lip 417, which has a smaller outside diameter than the first annular portion 416, to its distal end at tapered portion 419. Tapered portion 419 is tapered from its proximal end to its distal end and extends distally to the base 420, which is perpendicular, or substantially perpendicular, to the first annular portion 416.

Figure 19:
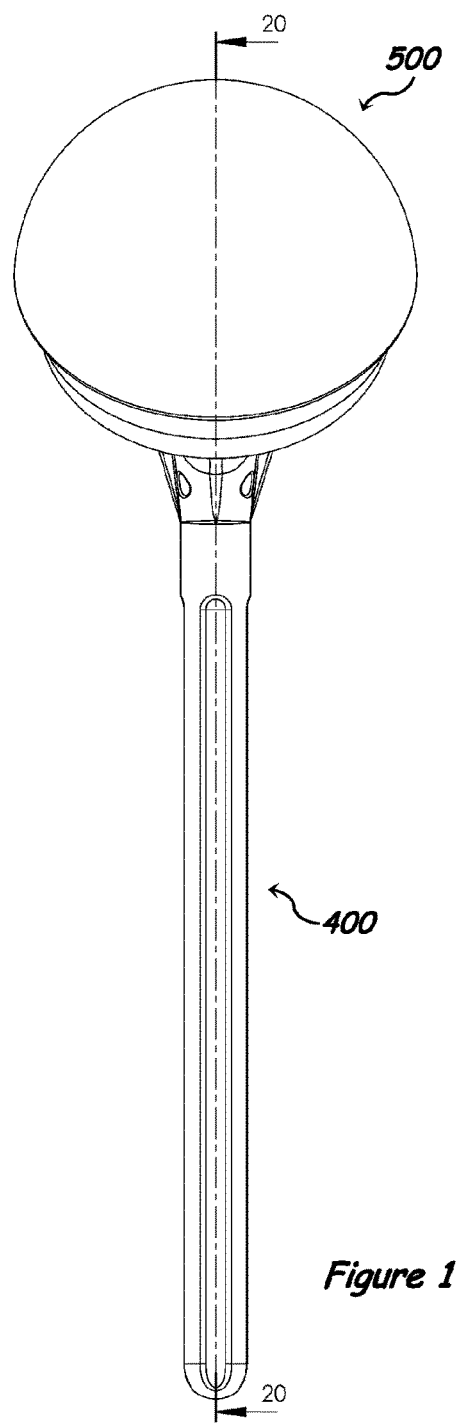
FIG. 19 is a front elevation view of the humeral head component illustrated in FIG. 17 attached to the humeral component illustrated in FIG. 15.

The proximal head 410 defines two recessed notches 422 that extend radially outward from the first annular portion 416 and away from the center of the cavity 414 and distally into the proximal head 410. The recessed notches 422 advantageously provide for substantially limiting, and/or substantially eliminating, the rotation of the humeral head component 500 when it is attached to the humeral component 400, as illustrated in FIGS. 19 and 20. While two recessed notches 422 having a substantially curved perimeter have been described and illustrated, any suitable number of recessed notches and configurations can be used, and skilled artisans will be able to select a suitable number of recessed notches, and configurations for the recessed notches, according to a particular embodiment based on various considerations, including the size of the humeral head component being used in conjunction with the humeral component, among others. Examples of suitable numbers of recessed notches include one, two, three, four, five and any number determined suitable for a particular application.

The humeral component 400 is formed of a ceramic, metal, or other suitable biocompatible material. Exemplary materials considered suitable for the humeral component 400 include titanium (Ti), and cobalt alloys (e.g., cobalt-chromium (CoCr), cobalt-chromium-molybdenum (Co-CrMo)). The humeral component 400 can comprise a single component. Alternatively, the humeral component 400 can comprise one or more components attached to one another. The humeral component 400 advantageously provides a component that serves as a universal platform that may be used with various modular components in the manner described herein to configure the humeral component 400 for use in a TSA or a RSA. Thus, once the humeral component 400 is implanted within a prepared proximal humerus of a patient, the humeral component 400 can be configured for a TSA as illustrated in FIGS. 1 through 3, a RSA as illustrated in FIGS. 21 through 23, or a hemi shoulder arthroplasty.

Figure 17:
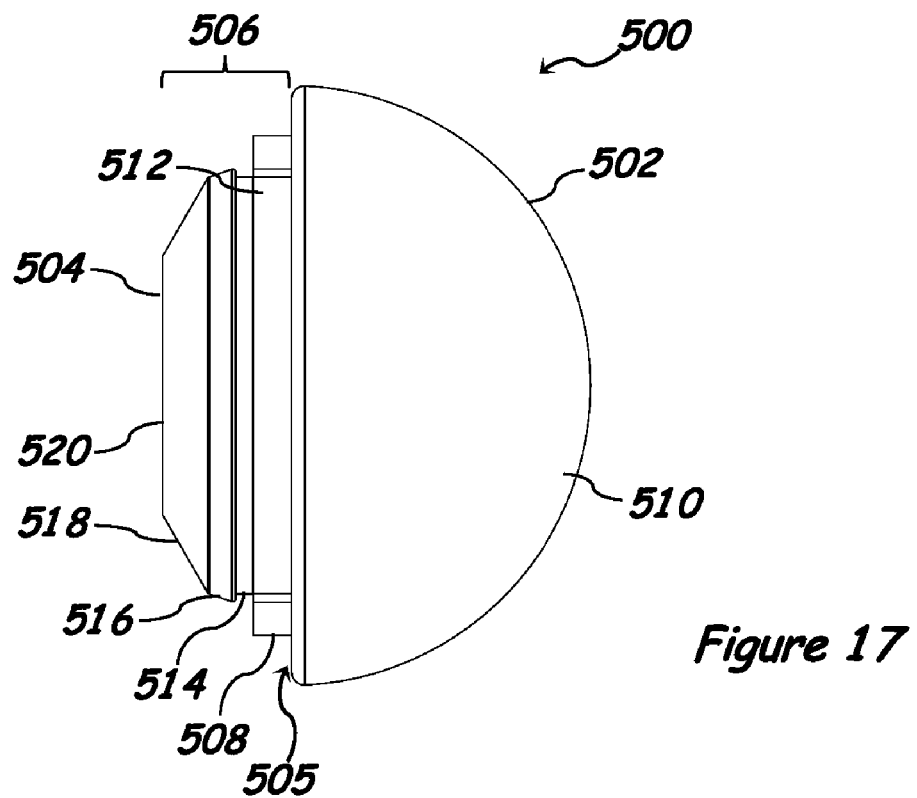
FIG. 17 is a side elevation view of an exemplary humeral head component.
Figure 18:
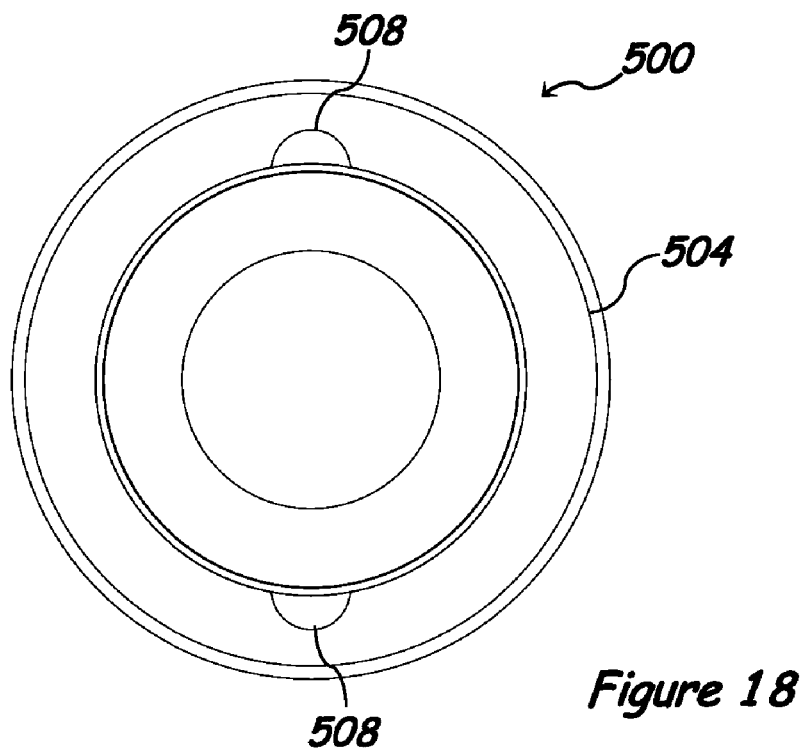
FIG. 18 is a rear elevation view of the humeral head component illustrated in FIG. 17.

FIGS. 17 and 18 illustrate an exemplary humeral head component 500 comprising a medial side 502, lateral side 504, projection 506, protuberances 508, and an articulating surface 510. The projection 506 is positioned on the lateral side 504 of the humeral head component 500, extends distally from the distal end 505 of the articulating surface 510, and comprises a first annular portion 512, recess 514, second annular portion 516, tapered portion 518, and base 520. The first annular portion 516 extends distally from the distal end 505 of the articulating surface 510 to recess 514, which extends radially inward towards the center of the projection 506. Distal to the recess 514 is second annular portion 516 that tapers from its proximal end at recess 514, which has a larger outside diameter than recess 514, to its distal end at tapered portion 518. Tapered portion 518 is tapered from its proximal end to its distal end and extends distally to the base 520 of the projection 506, which is perpendicular, or substantially perpendicular, to the first annular portion 512. Protuberances 508 extend outwardly from the first annular portion 512, away from the center of the projection 506, and are configured to be received by, and engage with, the recessed notches 422 of the humeral component 400.

The humeral head component 500 defines a convex anatomically shaped articulating surface 510 on the medial side 502 that articulates with the articulating surface 310 of the glenoid component 300 or with a natural glenoid. The articulating surface 510 can be provided in a variety of different radii and sizes, such as with varying diameters and varying heights to enable a surgeon to select an optimal humeral head component 500 needed for the anatomy of a particular patient. The articulating surface 510 is generally smooth, uninterrupted, and convex, or substantially convex. The geometry of the articulating surface 510 is configured to approximate, or replicate, the anatomy and structure of the head of a humerus of a patient (e.g., radius, thickness, length, width).

The humeral head component 500 is formed of ceramic, polyethylene or any other suitable biocompatible material. An exemplary material considered suitable for the humeral head component 500 is ultra-high-molecular-weight polyethylene (UHMWPE). While the humeral head component 500 has been described as formed of a ceramic, polyethylene, or other suitable biocompatible material, other materials are considered suitable, and skilled artisans will be able to select an appropriate material according to a particular embodiment based on various considerations, such as the intended use of the humeral head component, among others.

During use, the humeral head component 500 is attached to the humeral component 400 by using an interference fit between the projection 506 and cavity 414 with, or without, the use of cement. Protuberances 508 advantageously provide for substantially limiting, and/or substantially eliminating, the rotation of the humeral head component 500 when attached to the humeral component 400, as illustrated in FIGS. 19 and 20. While particular geometries have been described and illustrated with respect to the cavity 414 and projection 506, other geometries can be used, and skilled artisans will be able to select an appropriate geometry for a particular embodiment based on various considerations, including the geometry of the internal cavity of the humeral component and/or the geometry of the projection of the humeral head component. Examples of geometries considered suitable for the lateral side, projection, and/or protuberances of the humeral head component include geometries that mirror or substantially mirror the geometry of the internal cavity and recessed notches of the humeral component, and vise versa.

FIGS. 21 through 23 illustrate an exemplary RSA system 600 comprising a baseplate 200, a glenosphere component 700, a humeral component 400, and a humerosocket component 800. The baseplate 200 is similar to that described above with respect to FIGS. 4 through 7 and the humeral component 400 is similar to that described above with respect to FIGS. 15 and 16, unless otherwise described below. The baseplate 200 is configured to be received by, and attached to, a previously prepared glenoid of a patient and the glenosphere component 700 is configured to be received by, and attached to, the baseplate 200. The humeral component 400 is configured to be received by, and attached to, a previously prepared humerus of a patient and the humerosocket component 800 is configured to be received by, and attached to, the humeral component 400.

FIGS. 24 through 27 illustrate an exemplary glenosphere component 700 comprising proximal end 702, distal end 704, medial side 706, lateral side 708, base 707, circumferential, or substantially circumferential, wall 709, recess 710, raised geometry 711, toothed geometry 712, tapered cavity 714, articulating surface 716, bore 718, and retaining screw 720. On the medial side 706, the wall 709 and the base 707 cooperatively define a circumferential, or substantially circumferential, recess 710 extending from the medial side 706 towards the lateral side 708 and into the glenosphere component 700. The raised geometry 711 is disposed within recess 710, extends from the base 707 towards the medial side 706, and has an outer circumferential, or substantially circumferential, perimeter 705. The raised geometry 711 forms a toothed geometry 712 that extends about the entirety, or a portion, of the perimeter 705 and radially outward away from the center of the glenosphere component 700.

The toothed geometry 712 of the glenosphere component 700 is adapted to be received by, and engage with, the toothed geometry 212 of the baseplate 200 and is configured to compliment the toothed geometry of the 212 of the baseplate. The depth and length provided between each tooth of the toothed geometry 712, the number of teeth, and the angle at which the teeth are disposed on the perimeter 705 of the raised geometry 711 can vary, and skilled artisans will be able to select an appropriate configuration according to a particular embodiment based on various considerations, including the size of the baseplate and glenoid component.

The raised geometry 711 also has a convex, or substantially convex, portion 703 that extends proximally from the perimeter 705 and away from the base 707. The raised geometry 711 of the glenosphere component is adapted to be received by, and engage with, the geometry of the recess 210 of the baseplate 200. While portion 703 of the raised geometry 711 has been described and illustrated as being convex or substantially convex, the recess 710 has been described as being circumferential in configuration, and the raised geometry has been described as circumferential in configuration, any suitable geometry can be used, and skilled artisans will be able to select an appropriate geometry for a particular embodiment based on various considerations, including the geometry of the recess of the baseplate and/or the recess of the glenosphere component, among others. Examples of suitable geometries include flat, convex, and variating surfaces, among others. Examples of configurations for the recess, raised geometry, and/or outer perimeter that are considered suitable include a recess, raised geometry, and/or outer perimeter that partially extend around the circumference of the glenosphere component.

In addition, while the glenosphere component 700, or portions thereof, have been illustrated as circular, or substantially circular, other shapes are considered suitable, and skilled artisans will be able to select an appropriate shape for a glenosphere component according to a particular embodiment based on various considerations, including the anatomy of the patient, among others. Examples of shapes considered suitable include oval, oblong, rectangular and any shape determined suitable for a particular application.

The raised geometry 711 defines tapered cavity 714 and opening 715 of the tapered cavity 714 on portion 703. The tapered cavity 714 extends distally into the raised geometry 711 from opening 715 defined by raised geometry 711, defines a taper from the opening 715 to its base 717, and is adapted to receive the tapered trunnion 214 of the baseplate 200 (e.g., Morse taper) to attach the glenosphere component 700 to the baseplate 200. The tapered cavity 714 has a configuration complimentary to the tapered trunnion 214 of the baseplate 200.

The glenosphere component 700 defines an anatomically shaped, generally convex, articulating surface 716 on the lateral side 708 configured to articulate with a humerosocket component (e.g., 800). The articulating surface 716 defines a first opening 719 to bore 718, which extends through the gleno sphere component 700 to tapered cavity 714 allowing for the glenosphere component 700 to be attached to the baseplate 200 by retaining screw 720. The retaining screw 720 can be attached to, or provided separately from, the glenosphere component 700, and acts as a secondary means of attachment between the glenosphere component 700 and the baseplate 200. The proximal end of the retaining screw 720 is adapted to receive a tool used to assist with installing the baseplate 200 and/or glenosphere component 700 into the scapula of a patient.

The articulating surface 716 is generally smooth, uninterrupted, and convex, or substantially convex. The geometry of the articulating surface 716 can be provided in a variety of different radii and sizes, such as with varying diameters and varying heights to enable a surgeon to select an optimal glenosphere component 700 needed for the anatomy of a particular patient.

Figure 28:
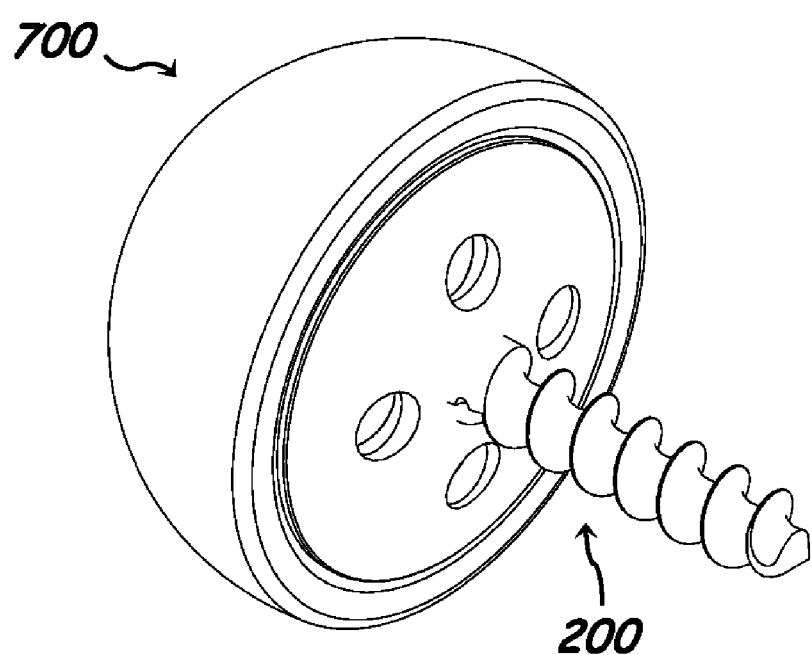
FIG. 28 is a perspective view of the glenosphere component illustrated in FIG. 24 attached to the baseplate illustrated in FIG. 4.
Figure 29:
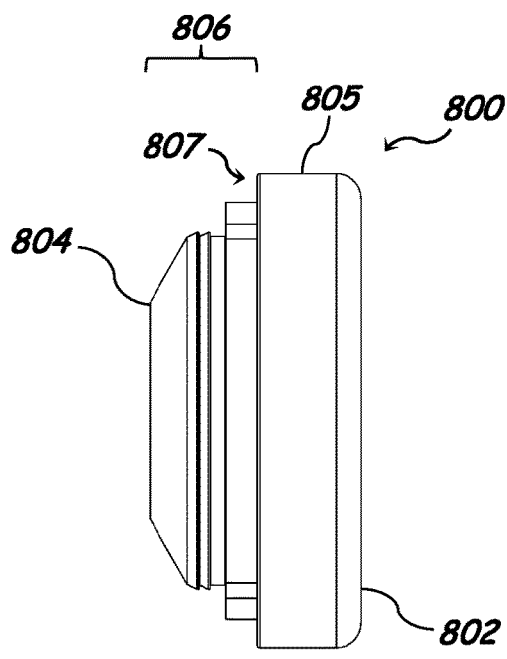
FIG. 29 is a side elevation view of an exemplary humerosocket component.
Figure 30:
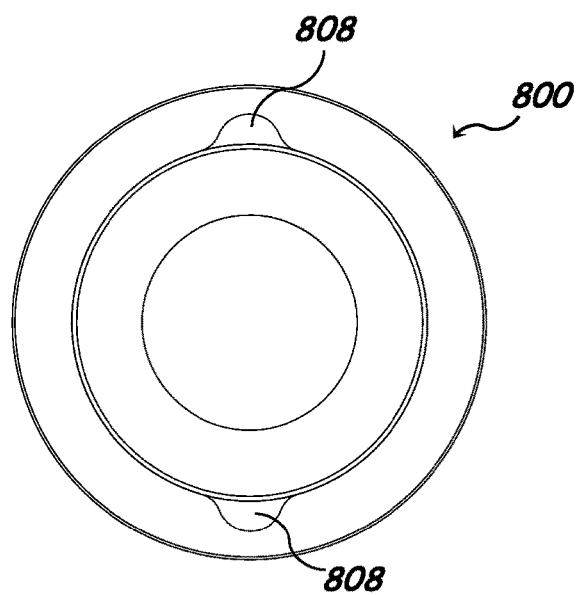
FIG. 30 is a rear elevation view of the humerosocket component illustrated in FIG. 29.
Figure 31:
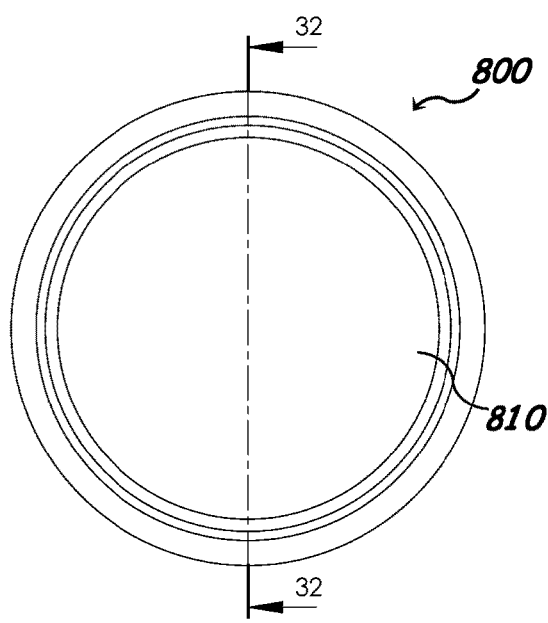
FIG. 31 is a front elevation view of the humerosocket component illustrated in FIG. 29.
Figure 32:
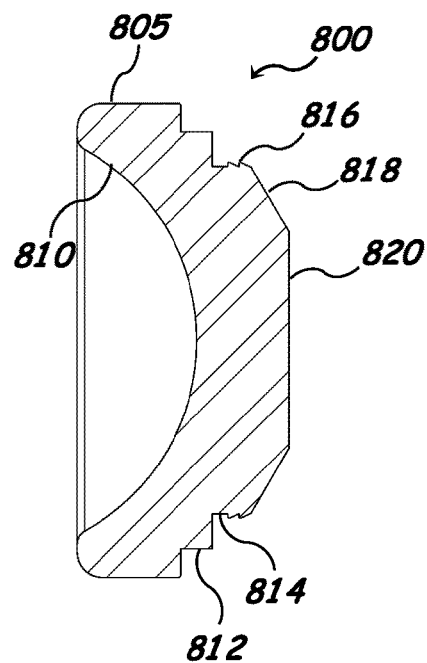
FIG. 32 is a cross-sectional view of the humerosocket component illustrated in FIG. 29, taken along line 32-32 in FIG. 31.

The toothed geometry 212 of the baseplate 200 and the toothed geometry 712 of the glenosphere component 700 are adapted to receive one another, and include a tolerance sufficient to allow the components to properly engage with one another, as illustrated in FIG. 28, which advantageously provides a combination of components (e.g., glenoid implant) that prevents rotation of the glenosphere component 700 when attached to the baseplate 200. In addition, the configuration of the toothed geometry 212 of the baseplate 200 and/or the toothed geometry 711 of the glenosphere component 700 advantageously provides for rotationally variable positioning of the glenosphere component 700 within the baseplate 200 when the two components are attached to one another.

The glenosphere component 700 is formed of a ceramic, metal, or other suitable biocompatible material. Exemplary materials considered suitable for the glenosphere component 700 include titanium (Ti), and cobalt alloys (e.g., cobalt-chromium (CoCr), cobalt-chromium-molybdenum (CoCrMo)). The glenosphere component 700 is configured to be attached to the baseplate 200 using an impact instrument that impacts the tapered trunnion 214 of the baseplate 200 into the tapered cavity 714 of the glenosphere component 700 creating a cold weld between the two components.

FIGS. 29 through 32 illustrate an exemplary humerosocket component 800 comprising a medial side 802, lateral side 804, first annular portion 805, projection 806, protuberances 808, and articulating face 810. The projection 806 is positioned on the lateral side 804 of the humerosocket component 800, extends distally from the distal end 807 of the first annular portion 805, and comprises a second annular portion 812, recess 814, ridges 816, tapered portion 818, and base 820. The second annular portion 812 extends distally from the distal end 807 of the first annular portion 805 to recess 814, which extends radially inward towards the center of the projection 806. Distal to the recess 814, and proximal to the tapered portion 818, are ridges 816 that extend outwardly away from the center of the projection 806 and are configured to provide a friction fit between the humerosocket component 800 and the humeral component 400 when the humerosocket component 800 is attached to the humeral component 400. Tapered portion 818 is tapered from its proximal end to its distal end and extends from the last ridge, or near the last ridge, distally to the base 820 of the projection 806, which is perpendicular or substantially perpendicular to the first annular portion 812. The protuberances 808 extend outwardly from the second annular portion 512, away from the center of the projection 806, and are configured to be received by the recessed notches 422 of the humeral component 400.

The humerosocket component 800 defines a concave articulating face 810 on medial side 802 that articulates with the articulating surface 716 of the glenosphere component 700. The articulating face 716 extends from the medial side 802 into the humerosocket component 800 towards the lateral side 804. The articulating face 810 can be provided in a variety of different radii and sizes, such as with varying diameters and varying heights to enable a surgeon to select an optimal humerosocket component 800 needed for the anatomy of a particular patient. The articulating surface 810 is generally smooth, uninterrupted, and concave, or substantially concave.

The humerosocket component 800 is formed of ceramic, polyethylene or any other suitable biocompatible material. An exemplary material considered suitable for the humerosocket component 800 is UHMWPE. While the humerosocket component 800 has been described as formed of a ceramic, polyethylene, or other suitable biocompatible material, other materials are considered suitable, and skilled artisans will be able to select an appropriate material according to a particular embodiment based on various considerations, such as the intended use of the humeral head component, among others.

During use, the humerosocket component 800 is attached to the humeral component 400 with, or without, the use of cement to provide a humeral implant. Protuberances 808 advantageously provide for substantially limiting, and/or substantially eliminating, the rotation of the humerosocket component 800 when attached to the humeral component 400, as illustrated in FIGS. 21 through 23. Furthermore, while particular geometries have been described and illustrated with respect to the projection 806, other geometries can be used, and skilled artisans will be able to select an appropriate geometry for a particular embodiment based on various considerations, including the geometry of the internal cavity of the humeral component. Examples of geometries considered suitable for the lateral side, projection, and/or protuberances include geometries that mirror or substantially mirror the geometry of the internal cavity and recessed notches of the humeral component.

The baseplate 200 advantageously provides for attaching either of the glenoid component 300 or glenosphere component 700 and humeral component 400 advantageously provides for attaching either of the humeral head component 500 or humerosocket component 800. The convertibility of the components allows for transitioning between a TSA and RSA system without requiring the replacement of the humeral component 400 and/or baseplate 200, providing for a procedure that is less complex, and requires less time to complete.

It is considered advantageous to provide a glenoid component 300 and/or glenosphere component 700 formed of metal (e.g., CoCrMo) to articulate with a humeral head component 500 and/or humerosocket component 800 formed of a plastic (e.g., UHMWPE) to provide improved wear properties of the components. For example, the inventor has determined that providing a humeral head component (e.g., humeral head component 500) formed of plastic (e.g., UHMWPE) is particularly well suited for use in a TSA or hemi shoulder arthroplasty at least because this material provides improved wear properties and reduces the likelihood of metal components coming into contact with other metal components. In addition, it is considered advantageous to provide a glenoid component 300 formed of metal (e.g., CoCrMo) to articulate with any form of humeral head component (e.g., natural, prosthetic) to provide improved wear properties of the components.

While various configurations have been described with respect to baseplate 200, glenoid component 300, and glenosphere component 700, it should be understood that other configurations are considered suitable. For example, inverting the configurations described with respect to baseplate 200, glenoid component 300, and glenosphere component 700 is considered suitable (e.g., the baseplate having a raised geometry with an outer circumferential perimeter forming a toothed geometry and the glenoid and/or glenosphere component having a circumferential wall forming a toothed geometry).

FIGS. 33 through 35 illustrate another exemplary glenosphere component 1000 similar to glenosphere component 700, except as described below, attached to another exemplary baseplate 900, similar to baseplate 200, except as described below. Baseplate 900 comprises a body 902, shaft 903, and threaded component 904. The body 902 is generally circular and comprises a medial side 906, lateral side 908, and defines a tapered cavity 910. The tapered cavity 910 extends from the lateral side 908 of the body 902 and into the body 902 towards the medial side 906, into a portion of shaft 903, and forms a taper from the lateral side 908 to the base 909 of the tapered cavity 910. The base 909 of the tapered cavity 910 defines a hexagonal recess 911, which is adapted to receive a tool used to assist with installing the baseplate 900 into the scapula of a patient. The shaft 903 has a diameter greater than the diameter of the threaded component 904 to assist with attachment of the component to the scapula of a patient.

The glenosphere component 1000 comprises medial side 1002, lateral side 1004, recess 1006, and tapered trunnion 1008. The glenoid component 1000 defines a circumferential, or substantially circumferential, recess 1006 on the medial side 1002 of the glenosphere component 1000 that extends into the glenosphere component 1000 from the proximal end 1003 of the glenosphere component 1000, and surrounds the tapered trunnion 1008. The tapered trunnion 1008 extends from the base 1007 of the recess 1006 and tapers as it extends away from the base 1007 of the recess 1006. The tapered trunnion 1008 is adapted to be received by and attach to the tapered cavity 910 of the baseplate 900 and includes ridge 1009 that is disposed along the length of the tapered trunnion 1008 and extends radially away from tapered trunnion 1008. It should be noted that ridge 1009 could be omitted.

While a particular geometry for recess 1006 and glenosphere component 1000 have been described and illustrated, skilled artisans will be able to select an appropriate geometry for the recess of the glenosphere component and glenosphere component according a particular embodiment based on various considerations, including the geometry of the baseplate, among others. Examples of shapes considered suitable include oval, oblong, rectangular and any shape determined suitable for a particular application. An example of s configuration for recess 1006 considered suitable includes a recess that extends around a portion of the circumference of the glenosphere component 1000.

The baseplate 900 and the glenosphere component 1000 are attached to one another through a cold weld between the components when the tapered trunnion 1008 of the glenosphere 1000 is received by, and attached to, the tapered cavity 910 of the baseplate 900. Optionally, a bore (not illustrated) can be provided to allow a length of a retaining screw to be inserted through the bore and provide a secondary means for attaching the glenosphere component 1000 to the baseplate 900.

The outside diameter 912 of the body 902 of the baseplate is configured to be smaller than the outside diameter 1010 of the recess 1006 so that bone grafting material can be inserted into the recess 1006 and assist with attaching the component to the scapula of a patient. This is considered advantageous because it allows for the bone grafting material that has been inserted within recess 1006 to become incorporated into the host bone, which aids in the stability of the components when implanted. Current RSA glenosphere components utilize a flat medial side which does not allow for additional bone grafting material to be incorporated into the component, such as glenosphere 1000. The depth of recess 1006 can vary, and skilled artisans will be able to select an appropriate depth according to a particular embodiment based on various considerations, including the configuration of the baseplate, among others.

A portion, or the entirety of, the medial side 906 of the baseplate 900, medial side 1002 of the glenosphere component 1000, and recess 1006 of the glenosphere component 1000 can be covered and/or filled with an osteoinductive material 1014. The osteoinductive material 1014 can comprise a highly porous biomaterial useful as a bone substitute and/or cell and tissue receptive material for promotion of bone in-growth to aid in the osseointegration of baseplate 900 and/or glenosphere component 1000 within the scapula of a patient and aids in the stability of the baseplate 900 and glenosphere component 1000. Such a material may be formed from a reticulated vitreous carbon foam substrate that is infiltrated and coated with a biocompatible metal (e.g., tantalum.) Osteoinductive material can be incorporated into any of the herein described components. For example, the humeral component (e.g., 400), humerosocket component (e.g., 800), humeral head component (e.g., 500), glenoid component (e.g., 300), glenosphere component (e.g., 700), and baseplate (e.g., 200) can all include osteoinductive material, and/or an osteoinductive surface (e.g., hydroxyapatite coating, trabecular metal), on a portion of, or the entirety of, the medial and/or lateral side of the component.

Glenosphere 1000 can alternatively be utilized as a humeral head component for a TSA or HSA. Current TSA and HSA humeral head replacements utilize a flat medial side which does not allow for additional bone grafting material to be incorporated into the component, such as glenosphere 1000. Skilled artisans will be able to select an appropriate use for the glenosphere component, and an appropriate means of attachment between the glenosphere and a humeral component, as described herein (e.g., tapered trunnion, tapered cavity), for integrating bone grafting material within the recess 1006 to provide for additional stability of the components.

In an alternative, glenosphere 1000 can be utilized as a glenoid implant without use of baseplate 900. For example, the tapered trunnion 1008 of the glenosphere component 1000 can be directly attached to a previously prepared scapula of a patient (e.g., a scapula having a tapered cavity with a recess slightly smaller than the size of the tapered trunnion of the glenosphere component), with, or without, the use of cement. In this example, the medial side 1002 of the glenosphere, and/or tapered trunnion 1008, can include a textured surface (e.g., one or more protuberances, bumps, groves, roughened surface), and/or an osteoinductive surface, in any configuration and/or combination to enhance the attachment, and/or bone ingrowth, of the glenosphere 1000 to the scapula of a patient. Furthermore, recess 1006 can be utilized to increase stability of the attachment to the scapula of a patient (e.g., by preparing the scapula to have portions thereof received within recess 1006), or recess 1006 can be omitted. In another example, the tapered trunnion 1008 can include one or more annular ribs, protuberances, and/or raised surfaces (not shown) to increase stability of the component when attached to a previously prepared scapula of a patient. In a further example, the tapered trunnion 1008 can be replaced by another means of attachment (e.g., threaded component, attachment peg).

Figures 36, 37:
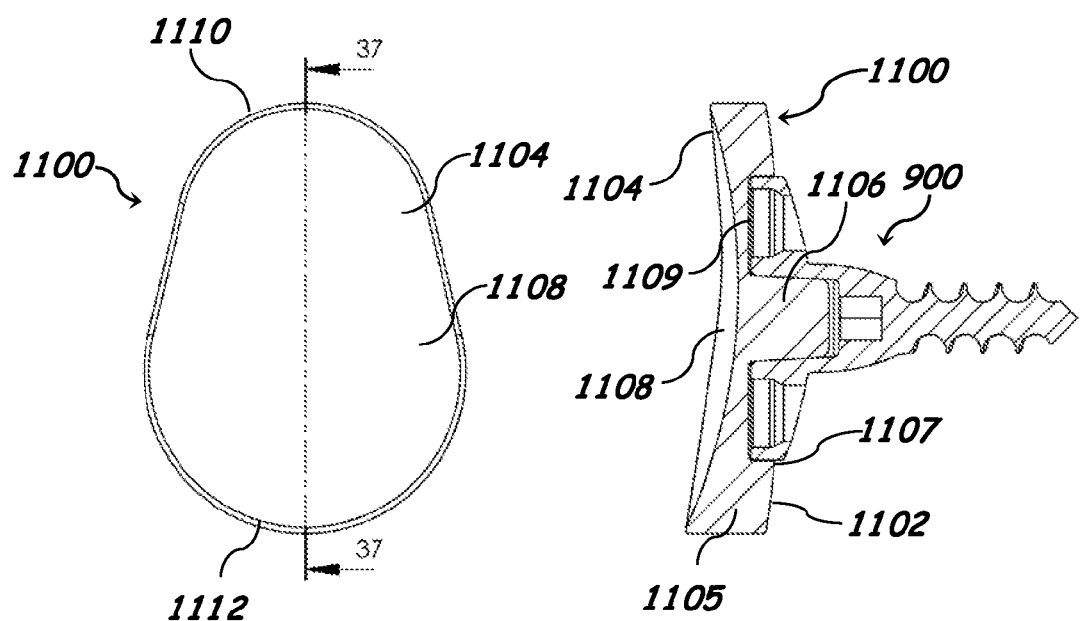
FIG. 36 is a front elevation view of another exemplary glenoid component attached to the baseplate illustrated in FIG. 33.
FIG. 37 is a cross-sectional view of the glenoid component illustrated in FIG. 36 attached to the baseplate illustrated in FIG. 33, taken along line 37-37 in FIG. 36.

FIGS. 36 and 37 illustrate another exemplary glenoid component 1100, which is similar to glenoid component 300, except as described below, attached to baseplate 900. The glenoid component 1100 comprises a medial side 1102, lateral side 1104, body 1105, tapered trunnion 1106, recess 1107 and an articulating surface 1108. The body 1105 of the glenoid component 1100 has a generally oval shape with a first end 1110 having a radius that is smaller than the radius of an opposing second end 1112. Body 1105 defines circumferential, or substantially circumferential, recess 1107 which extends from the medial side 1102 towards the lateral side 1104. The tapered trunnion 1106 extends from the base 1109 of recess 1107 towards the medial side 1102, tapers from base 1009 to its proximal end, and is adapted to be received and attached to the tapered cavity 910 of the baseplate 900. Recess 1107 is adapted to receive a portion, or the entirety of, the body 902 of the baseplate 900. The medial side 906 of the baseplate and medial side 1102 of the glenoid component 1100 can comprise an osteoinductive surface and/or material to assist with glenoid fixation.

In an alternative, glenoid component 1100 can be utilized as a glenoid implant without use of baseplate 900. For example, the tapered trunnion 1106 of the glenoid component 1100 can be directly attached to a previously prepared scapula of a patient (e.g., a scapula having a tapered cavity with a recess slightly smaller than the size of the tapered trunnion of the glenoid component), with, or without, the use of cement. In this example, the medial side 1102 of the glenoid component, and/or tapered trunnion 1106, can include a textured surface (e.g., one or more protuberances, bumps, groves, roughened surface), and/or an osteoinductive surface, in any configuration and/or combination to enhance the attachment, and/or bone ingrowth, of the glenoid component 1100 to the scapula of a patient. Furthermore, recess 1107 can be utilized to increase stability of the attachment to the scapula of a patient (e.g., by preparing the scapula to have portions thereof received within recess 1107), or recess 1107 can be omitted. In another example, the tapered trunnion 1106 can include one or more annular ribs, protuberances, and/or raised surfaces (not shown) to increase stability of the component when attached to a previously prepared scapula of a patient. In a further example, the tapered trunnion 1106 can be replaced by another means of attachment (e.g., threaded component, attachment peg).

The distance from about the outside diameter of the medial side 906 of the body 902 to about the center of concavity of the articulating surface 1108 can vary according to the desired result of the procedure being conducted, and the amount of the baseplate received within the recess of the glenoid component can also vary, and skilled artisans will be able to select an appropriate distance according to a particular embodiment based on various considerations, such as the anatomy of the patient. Exemplary distances considered suitable between about the center of the concavity of the articulating surface 1108 and about the outer diameter of the medial side 906 of the body 902 include distances in the range from about 1 mm to about 6 mm. Additional exemplary distances considered suitable between about the center of the concavity of the articulating surface 1108 and about the outer diameter of the medial side 906 of the body 902 include distances in the range from about 2 mm to about 5 mm. Further exemplary distances considered suitable between about the center of the concavity of the articulating surface 1108 and about the outer diameter of the medial side 906 of the body 902 include distances in the range from about 2.5 mm to about 4.5 mm. Additional exemplary distances considered suitable between about the center of the concavity of the articulating surface 1108 and about the outer diameter of the medial side 906 of the body 902 include distances about 3 mm. The distances described above can alternatively be calculated from the about the proximal end of the glenoid component 1100, or the medial side 906 of the outside diameter 912 of the body 902 when the glenoid component 1100 is attached to the baseplate 900, to about the center of the concavity of the articulating surface 1108. In addition, the distances described above can apply to the glenoid implant illustrated in FIGS. 12 through 14.

Figure 38:
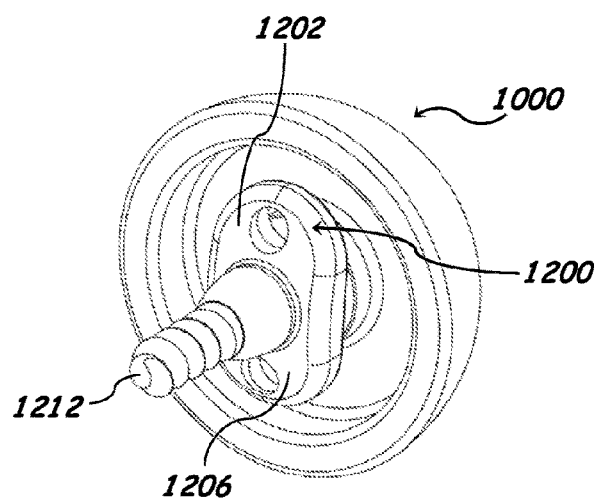
FIG. 38 is a perspective view of the glenosphere component illustrated in FIG. 33 attached to another exemplary baseplate.
Figures 39, 40:
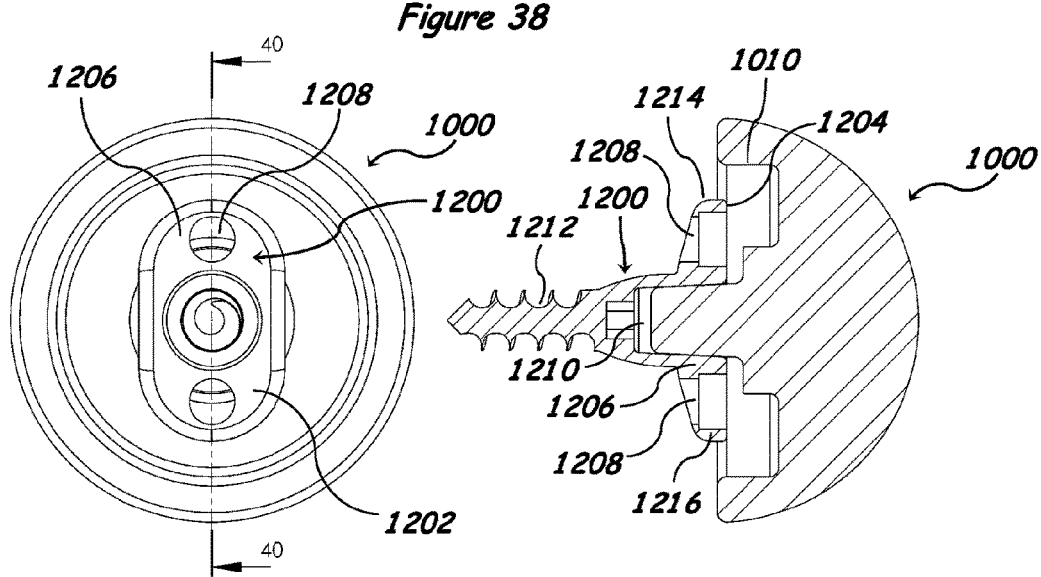
FIG. 39 is a rear elevation view of the glenosphere component illustrated in FIG. 33 attached to the baseplate illustrated in FIG. 38.
FIG. 40 is a cross-sectional view of the glenosphere component illustrated in FIG. 33 attached to the baseplate illustrated in FIG. 38, taken along line 40-40 in FIG. 39.
Figure 44:
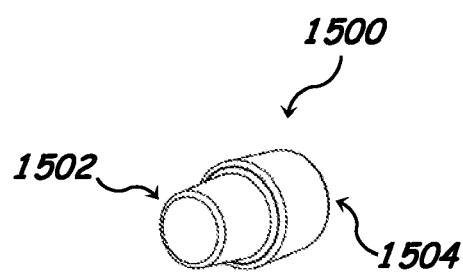
FIG. 44 is a perspective view of an exemplary connector.
Figure 45:
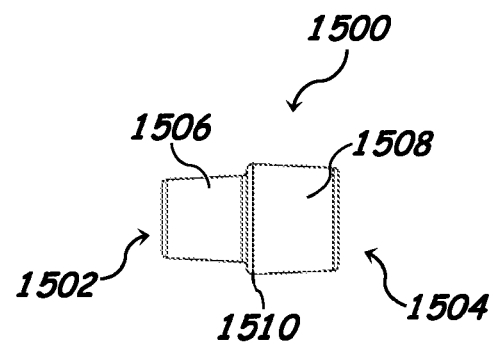
FIG. 45 is a side elevation view of the connector illustrated in FIG. 44.
Figure 46:
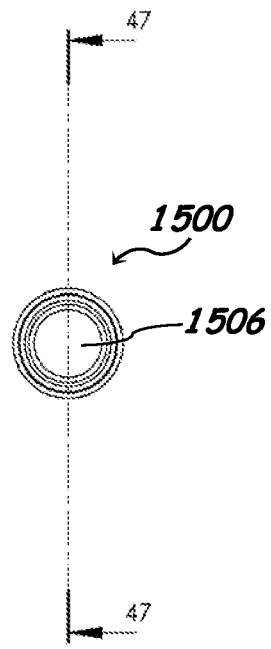
FIG. 46 is a rear elevation view of the connector illustrated in FIG. 44.
Figure 47:
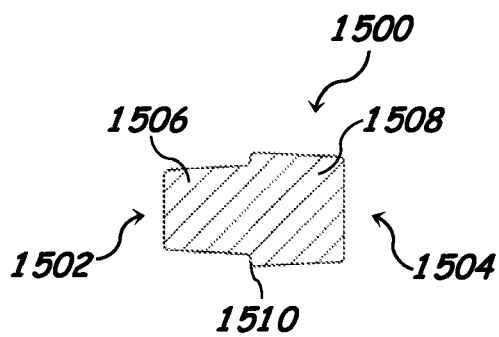
FIG. 47 is a cross-sectional view of the connector illustrated in FIG. 44, taken along line 47-47 in FIG. 46.

FIGS. 38 through 40 illustrate glenosphere component 1000 attached to another exemplary baseplate 1200, which is similar to baseplate 1100, except as described below. The baseplate 1200 comprises a medial side 1202, lateral side 1204, body 1206, bores 1208, internal cavity 1210, and threaded component 1212. The body 1206 comprises an oblong configuration having a first end 1214 and an opposably positioned second end 1216. The distance between the first end 1214 and the second end 1216 is smaller than the outside diameter 1010 of the recess 1006 of the glenosphere component 1000 so that bone grafting material can be inserted into the recess 1006 and attach to the scapula of a patient. The medial side 906 of the baseplate and medial side 1202 of the glenoid component 1200 can comprise an osteoinductive surface and/or material to assist with glenoid fixation.

It is considered advantageous to provide an oblong configuration to maximize the amount of bone grafting material that can be incorporated into the recess 1006 of the glenosphere component and increase the surface area of the osteoinductive material that can contact the prepared scapula of a patient allowing for increased stability of the components. Furthermore, the oblong configuration advantageously simplifies the procedure associated with attaching the baseplate 1100 to a prepared scapula of a patient.

FIGS. 41 through 43 illustrate another exemplary glenosphere component 1300, which is similar to glenosphere component 1000, except as described below, attached to another exemplary baseplate 1400, which is similar to baseplate 1200, except as described below.

The glenosphere component 1300 comprises a medial side 1302, lateral side 1304, recess 1306, and tapered cavity 1308. The medial side 1302 defines recess 1306 and further defines tapered cavity 1308 within recess 1306. As an alternative to the tapered trunnion 1008 of glenosphere 1000, glenosphere 1300 defines a tapered cavity 1308 defined by the body of the glenosphere 1300, which extends from ridge 1310 into glenosphere component 1300, and is adapted to receive the tapered trunnion 1408 of the baseplate. Alternatively, ridge 1310 can be omitted and tapered cavity 1308 can extend from the base of the recess 1306 into the glenosphere component 1300.

Glenosphere 1300 can alternatively be utilized as a humeral head component for a TSA or HSA. Current TSA and HSA humeral head replacements utilize a flat medial side which does not provide recess 1306 allowing for additional bone grafting material to be utilized. Skilled artisans will be able to select an appropriate use for the glenosphere component, and an appropriate means of attachment between the glenosphere and a humeral component, as described herein (e.g., tapered trunnion, tapered cavity), for integrating bone grafting material within the recess 1306 to provide for additional stability of the components.

Baseplate 1400 comprises a body 1402, bores 1404, tapered trunnion 1406, and threaded component 1408. As an alternative to the tapered cavity 910 in baseplate 900 and internal cavity 1205 in baseplate 1200, the body 1402 of baseplate 1400 defines a tapered trunnion 1406 that extends distally from the lateral side 1403 of the body 1402. The tapered trunnion 1406 defines a hexagonal recess 1410 used to attach the baseplate 1400 to a prepared scapula of a patient. The tapered trunnion 1408 is adapted to be received by, and attached to, the tapered cavity 1308 of the glenosphere component 1300.

Each of the baseplates, glenoid components, and/or glenosphere components described herein can include a tapered trunnion, tapered cavity, and/or bore to attached the component to a baseplate. For example, a baseplate can comprise a tapered trunnion and an associated glenoid component or glenosphere component can comprise a tapered cavity. In another example, a baseplate can comprise a tapered cavity and an associated glenoid component or glenosphere component can comprise a tapered trunnion. In another example, the baseplate can comprise a tapered cavity and an associated glenoid component or glenosphere component can comprise a tapered cavity and a connecter can be used to attached the components, as described below.

FIGS. 44 through 47 illustrate an exemplary connector 1500 comprising a proximal end 1502, distal end 1504, first portion 1506, second portion 1508, and lip 1510. The first portion 1506 extends from the proximal end 1502 to the lip 1510 and is tapered from the lip 1510 to the proximal end 1502. The second portion 1508 extends from the distal end 1504 to the lip 1510 and is tapered from the lip 1510 to the distal end 1504. The outside diameter of the second portion 1508 at lip 1510 is larger than the outside diameter of the first portion 1506 at lip 1510. While the outside diameter of the second portion 1508 at lip 1510 is described and illustrated as larger than the outside diameter of the first portion 1506 at lip 1510, the outside diameter of the first portion and second portion can be equal and the lip can define an outside diameter larger than the outside diameter of the first and second portion. Skilled artisans will be able to select an appropriate size for the first portion, second portion, and/or lip according to a particular embodiment based on various considerations, including the configuration of the tapered cavity for which the connector will be used.

The connector 1500 advantageously provides a double trunnion connector, which can be used to attach one or more of the various components described herein, or other various components (e.g., off the shelf components). For example, the connector 1500 can be used to attach glenosphere component 1300 having tapered cavity 1308 to baseplate 900 having tapered cavity 910. In another example, the connector 1400 can be used to attach a glenoid component having a tapered cavity to a baseplate 900 having a tapered cavity 910. The connector 1500 is adapted to be received by and create a cold weld with the tapered cavity of the component that will be attached thereto.

FIGS. 48 through 50 illustrate another exemplary glenosphere component 1600 attached to baseplate 900 using connector 1500. Glenosphere 1600 is similar to glenosphere 1000, except as described below. Glenosphere 1600 comprises medial side 1602, lateral side 1604, recess 1606, circumferential, or substantially circumferential, wall 1607, tapered cavity 1608, and articulating surface 1610. The body 1605 of the glenosphere component 1600 defines recess 1606, which extends from medial side 1602 towards the lateral side 1604, and is adapted to receive a portion of, or the entirety of, body 902 of the baseplate 900. Wall 1607 is configured to surround a portion of, or the entirety of, body 902 of the baseplate 900. Tapered cavity 1608 is defined by body 1605 within recess 1606, extends from the base of recess 1606 towards lateral side 1604, and is adapted to receive a portion of the connector 1500. The opposing end of the connector is received by the tapered cavity 910 of the baseplate 900. Connector 1500 advantageously provides for use with an off the shelf component, such as an off the shelf glenosphere component.

Figure 51:
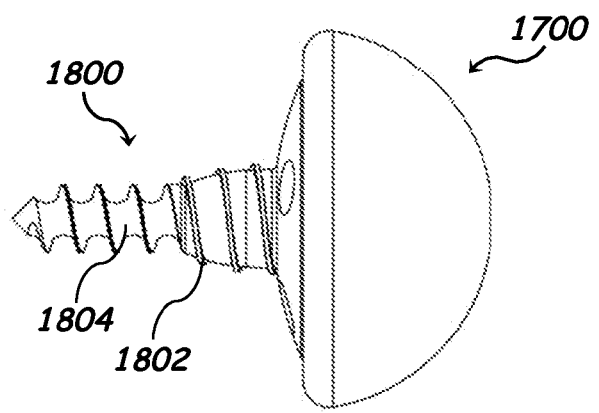
FIG. 51 is a side elevation view of another exemplary glenosphere component attached to another exemplary baseplate using an exemplary adaptor.
Figure 52:
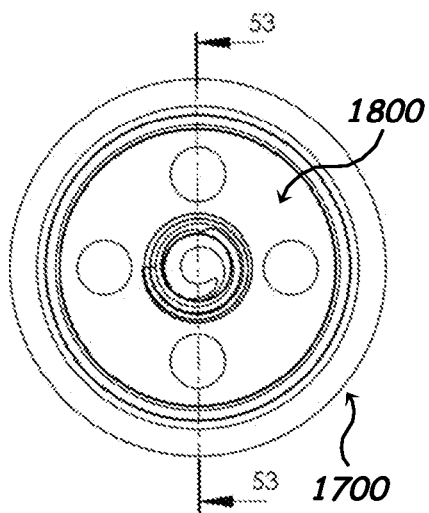
FIG. 52 is a rear elevation view of the glenosphere component illustrated in FIG. 51 attached to the baseplate illustrated in FIG. 51 using an exemplary adaptor.
Figure 53:
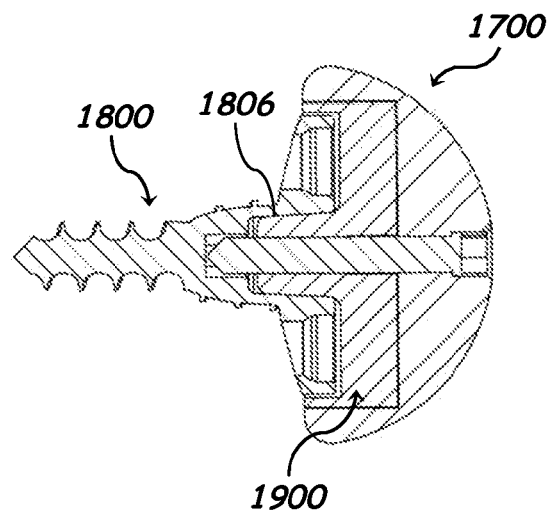
FIG. 53 is a cross-sectional view of the glenosphere component illustrated in FIG. 51 attached to the baseplate illustrated in FIG. 51 using an exemplary adaptor, taken along line 53-53 in FIG. 52.
Figure 54:
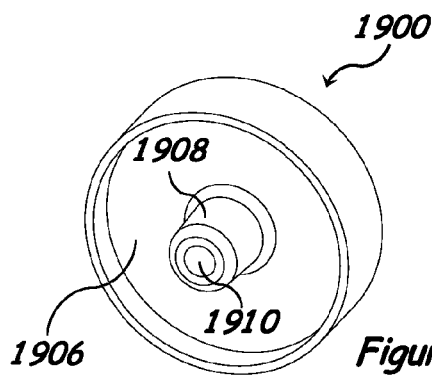
FIG. 54 is a perspective view of the adaptor illustrated in FIG. 53.
Figure 55:
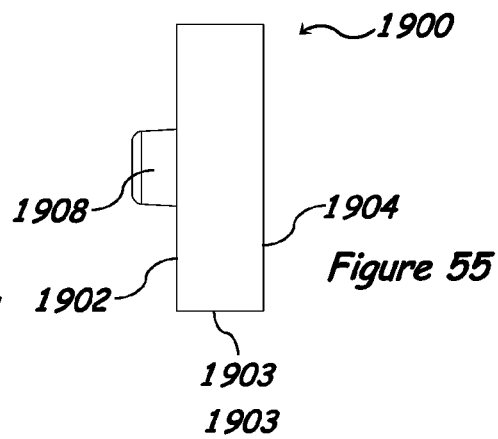
FIG. 55 is a side elevation of the adaptor illustrated in FIG. 53.
Figure 56:
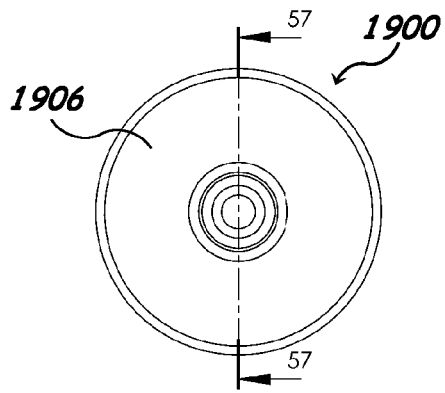
FIG. 56 is a rear elevation of the adaptor illustrated in FIG. 53.
Figure 57:
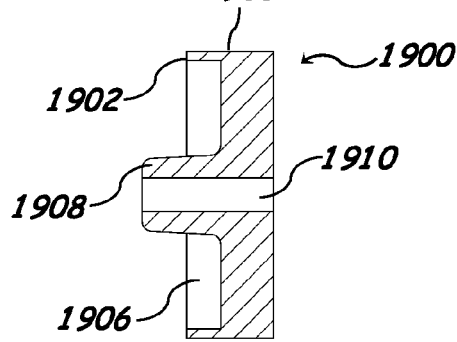
FIG. 57 is a cross-sectional view of the adaptor illustrated in FIG. 53, taken along line 57-57 in FIG. 56.
Figure 58:
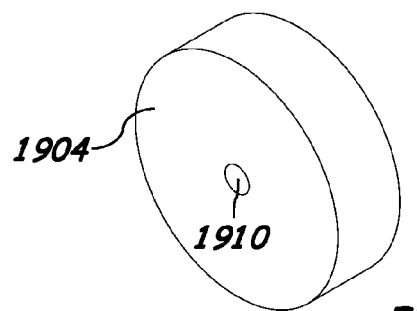
FIG. 58 is another perspective view of the adaptor illustrated in FIG. 53.
Figure 59:
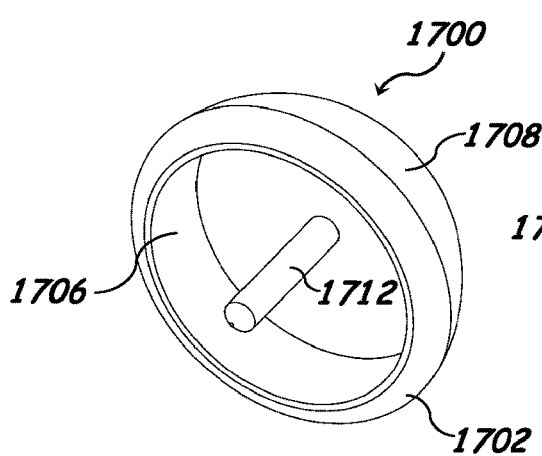
FIG. 59 is a perspective view of the glenosphere component illustrated in FIG. 51.
Figure 60:
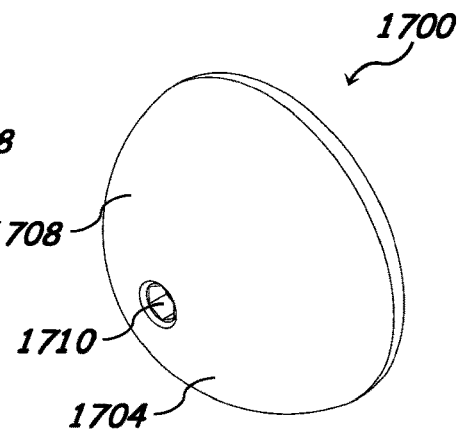
FIG. 60 is another perspective view of the glenosphere component illustrated in FIG. 51.
Figure 61:
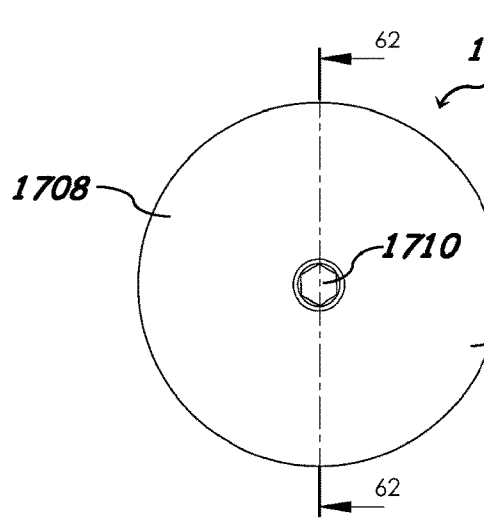
FIG. 61 is a front elevation view of the glenosphere component illustrated in FIG. 51.
Figure 62:
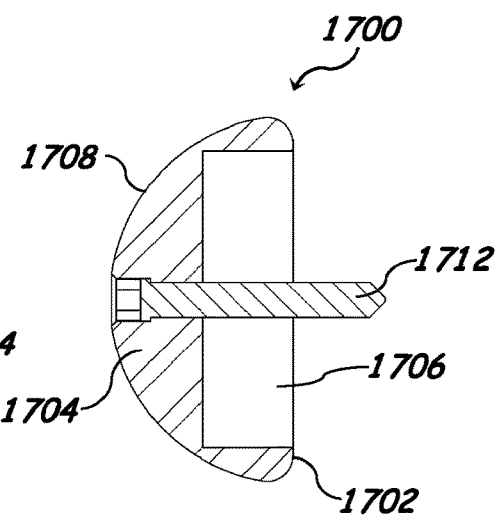
FIG. 62 is a cross-sectional view of the glenosphere component illustrated in FIG. 51, taken along line 62-62 in FIG. 61.
Figure 63:
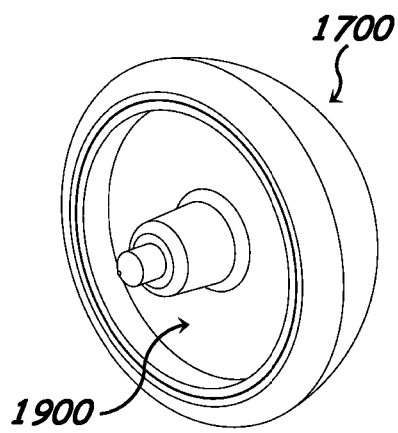
FIG. 63 is a perspective view of the glenosphere component illustrated in FIG. 51 attached to the adaptor illustrated in FIG. 53.
Figure 64:
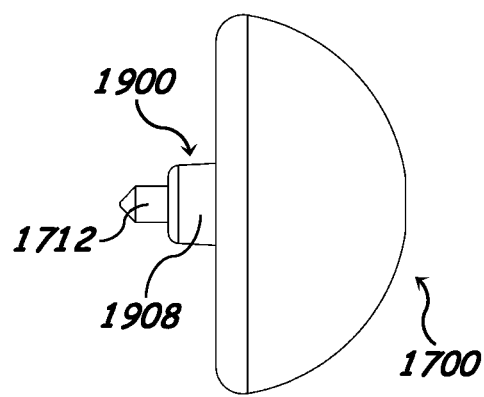
FIG. 64 is a side elevation view of the glenosphere component illustrated in FIG. 51 attached to the adaptor illustrated in FIG. 53.
Figure 65:
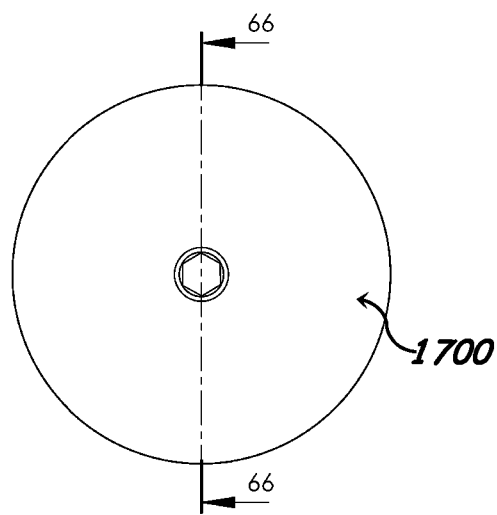
FIG. 65 is a front elevation view of the glenosphere component illustrated in FIG. 51 attached to the adaptor illustrated in FIG. 53.
Figure 66:
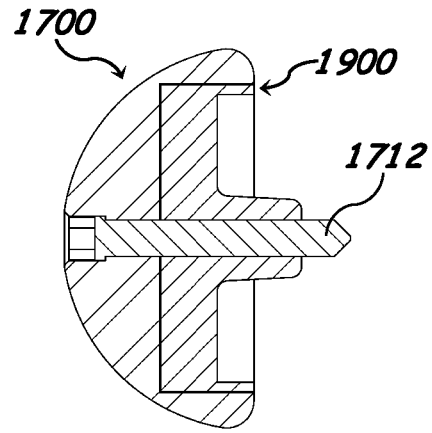
FIG. 66 is a cross-sectional view of the glenosphere component illustrated in FIG. 51 attached to the adaptor illustrated in FIG. 53, taken along line 66-66 in FIG. 65.
Figure 67:
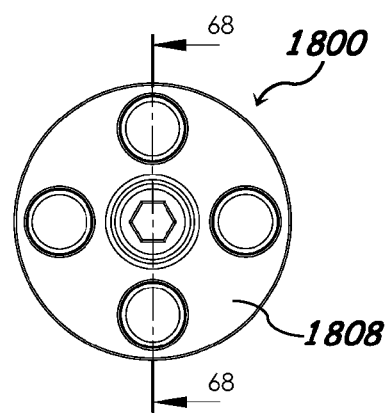
FIG. 67 is a front elevation view of the baseplate illustrated in FIG. 51.
Figure 68:
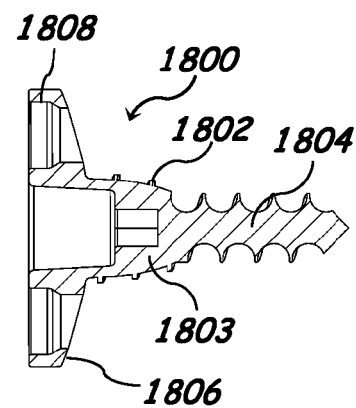
FIG. 68 is a cross-sectional view of the baseplate illustrated in FIG. 51, taken along line 68-68 in FIG. 67.
Figure 69:
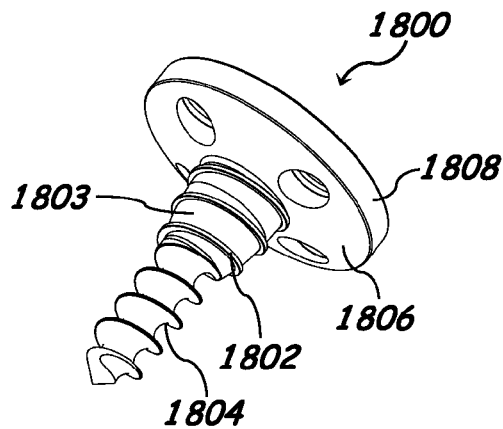
FIG. 69 is a perspective view of the baseplate illustrated in FIG. 51.
Figure 70:
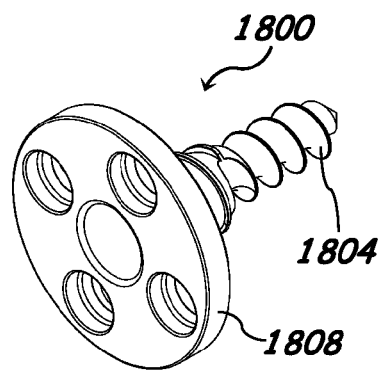
FIG. 70 is another perspective view of the baseplate illustrated in FIG. 51.

FIGS. 51 through 53 illustrate another exemplary glenosphere component 1700 attached to another exemplary baseplate 1800 using an exemplary adaptor 1900. Glenosphere component 1700, illustrated in FIGS. 59 through 62, comprises medial side 1702, lateral side 1704, body 1703, recess 1706, articulating surface 1708, bore 1710, and retaining screw 1712. The body 1703 of the glenosphere component 1700 defines a circumferential, or substantially circumferential, recess that extends from the medial side 1702 towards the lateral side 1704, and is adapted to receive a portion of, or the entirety of, adaptor 1900. Bore 1710 extends through glenosphere component 1700 from the lateral side 1704 to the medial side 1702 and allows for securing the retaining screw 1712 to the baseplate 1800.

Baseplate 1800, illustrated in FIGS. 67 through 70, is similar to baseplate 900, except that threads 1802 are provided along the entire, or substantially the entirety of, shaft 1803 of the threaded component 1804. The threads extend from the medial side 1806 of the body 1808 to the proximal end of the threaded component 1804. This configuration advantageously assists with securing the baseplate 1800 to the prepared scapula of a patient.

Adaptor 1900, illustrated in FIGS. 54 through 58, comprises medial side 1902, lateral side 1904, recess 1906, tapered trunnion 1908, and bore 1910. The body 1903 of the adaptor 1900 is generally circular and has an outside diameter that is adapted to be received by the recess 1706 of the glenosphere component 1700. The body 1903 of the adaptor 1900 defines a circumferential, or substantially circumferential, recess 1706 that extends distally into the body of the adaptor 1900 from the medial side 1902 towards the lateral side 1904, and is adapted to receive a portion of, or the entirety of, the body 1808 of the baseplate 1800. Tapered trunnion 1908 is defined by the body 1903, extends proximally from the base of the recess 1906, defines a taper from the base of the recess 1906 to its proximal end, and is adapted to be received by the tapered cavity 1806 of the baseplate 1800. Bore 1910 extends through body 1903 of the adaptor 1900 and tapered trunnion 1908, and is adapted to receive a length of retaining screw 1712. Adaptor 1900 advantageously provides for use with an off the shelf component, such as an off the shelf glenosphere component.

While the adaptor 1900, or portions thereof, have been illustrated as circular, or substantially circular, other shapes are considered suitable, and skilled artisans will be able to select an appropriate shape for an adaptor according to a particular embodiment based on various considerations, including the geometry of the baseplate, among others. Examples of shapes considered suitable include oval, oblong, rectangular and any shape determined suitable for a particular application.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed is:

1. A reverse shoulder prosthesis system, comprising:
 a baseplate comprising:
  a body having an oblong configuration and including:
   a lateral side,
   a medial side,
   a first end comprising a first bore extending through the body from the lateral side to the medial side; and
   a second end positioned opposite the first end and comprising a second bore extending through the body from the lateral side to the medial side, the first end and the second end defining the oblong configuration;
  a threaded component; and
  a shaft having a hydroxyapatite coating positioned between the body and the threaded component;
 a glenosphere component comprising:
  a medial side including a recess configured to receive at least the lateral side of the baseplate body such that the first end and the second end of the baseplate body is positioned in the recess;
  a lateral side; and
  a tapered trunnion;
 a humerosocket component comprising:
  a medial side;
  a lateral side;
  a projection positioned on the lateral side of the humerosocket component; and
  an articulating face defined in the medial side of the humerosocket component and configured to receive the lateral side of the glenosphere component; and
 a humeral component comprising:
  a distal stem configured to be fitted within a prepared proximal end of a humerus of a patient;
  a transition region including an aperture extending through a portion of the transition region; and
  a proximal head defining a cavity extending distally into the proximal head, the cavity configured to receive the projection of the humerosocket component.

2. The reverse shoulder prosthesis system of claim 1, wherein the first end of the baseplate body and the second end of the baseplate body span a distance that is smaller than an outside diameter of the recess in the medial side of the glenosphere component.

3. The reverse shoulder prosthesis system of claim 1, wherein at least a portion of the recess in the medial side of the glenosphere component is configured to receive bone grafting material.

4. The reverse shoulder prosthesis system of claim 1, wherein the medial side of the baseplate body comprises an osteoinductive surface.

5. The reverse shoulder prosthesis system of claim 1, wherein the medial side of the glenosphere component comprises an osteoinductive surface.

6. The reverse shoulder prosthesis system of claim 1, wherein the baseplate body further comprises a tapered cavity extending from the lateral side into the baseplate body.

7. The reverse shoulder prosthesis system of claim 6, further comprising a hexagonal recess formed in a base of the tapered cavity.

8. The reverse shoulder prosthesis system of claim 7, wherein the hexagonal recess is configured to receive a baseplate installation tool.

9. The reverse shoulder prosthesis system of claim 1, wherein the humerosocket component further comprises an annular portion, and the projection comprises a tapered portion.

10. The reverse shoulder prosthesis system of claim 9, wherein the tapered portion extends to a base of the lateral side of the humerosocket component.

11. A method of using a reverse shoulder prosthesis system, the method comprising:
 attaching a baseplate to a scapula of a patient, the baseplate comprising:
  a body having an oblong configuration and including:
   a lateral side,
   a medial side,
   a first end comprising a first bore extending through the body from the lateral side to the medial side; and
   a second end positioned opposite the first end and comprising a second bore extending through the body from the lateral side to the medial side, the first end and the second end defining the oblong configuration;
  a threaded component; and
  a shaft having a hydroxyapatite coating positioned between the body and the threaded component;
 attaching a glenosphere component to the baseplate, the glenosphere component comprising:
  a medial side including a recess configured to receive at least the lateral side of the baseplate body such that the first end and the second end of the baseplate body is positioned in the recess;
  a lateral side; and
  a tapered trunnion;
 attaching a humeral component to a humerus of the patient, the humeral component comprising:
  a distal stem configured to be fitted within a prepared proximal end of the humerus of the patient;
  a transition region including an aperture extending through a portion of the transition region; and
 a proximal head defining a cavity extending distally into the proximal head, the cavity configured to receive a projection of a humerosocket component; and
 attaching the humerosocket component to the humeral component, the humerosocket component comprising:
  a medial side;
  a lateral side;
  a projection positioned on the lateral side of the humerosocket component; and
  an articulating face defined in the medial side of the humerosocket component and configured to receive the lateral side of the glenosphere component.

12. The method of claim 11, wherein the first end of the baseplate body and the second end of the baseplate body span a distance that is smaller than an outside diameter of the recess in the medial side of the glenosphere component.

13. The method of claim 11, further comprising depositing bone grafting material in at least a portion of the recess in the medial side of the glenosphere component.

14. The method of claim 11, wherein the medial side of the baseplate body comprises an osteoinductive surface.

15. The method of claim 11, wherein the medial side of the glenosphere component comprises an osteoinductive surface.

16. The method of claim 11, wherein the baseplate body further comprises a tapered cavity extending from the lateral side into the baseplate body.

17. The method of claim 16, further comprising a hexagonal recess formed in a base of the tapered cavity.

18. The method of claim 17, wherein attaching the baseplate to the scapula of the patient is performed at least in part by inserting a baseplate installation tool into the hexagonal recess.

19. The method of claim 11, wherein the humerosocket component further comprises an annular portion, and the projection comprises a tapered portion.

20. A method of manufacturing a reverse shoulder prosthesis system, the method comprising:
  forming a baseplate comprising:
    a body having an oblong configuration and including:
      a lateral side,
      a medial side,
      a first end comprising a first bore extending through the body from the lateral side to the medial side; and
      a second end positioned opposite the first end and comprising a second bore extending through the body from the lateral side to the medial side, the first end and the second end defining the oblong configuration;
    a threaded component; and
    a shaft having a hydroxyapatite coating positioned between the body and the threaded component;
  forming a glenosphere component comprising:
    a medial side including a recess configured to receive at least the lateral side of the baseplate body such that the first end and the second end of the baseplate body is positioned in the recess;
    a lateral side; and
    a tapered trunnion;
  forming a humerosocket component comprising:
    a medial side;
    a lateral side;
    a projection positioned on the lateral side of the humerosocket component; and
    an articulating face defined in the medial side of the humerosocket component and configured to receive the lateral side of the glenosphere component; and
  forming a humeral component comprising:
    a distal stem configured to be fitted within a prepared proximal end of a humerus of a patient;
    a transition region including an aperture extending through a portion of the transition region; and
    a proximal head defining a cavity extending distally into the proximal head, the cavity configured to receive the projection of the humerosocket component.

* * * * *